(12) United States Patent
Zhao et al.

(10) Patent No.: US 11,148,389 B2
(45) Date of Patent: Oct. 19, 2021

(54) HYDROGEL-ELASTOMER HYBRIDS

(71) Applicant: Massachusetts Institute of Technology, Cambridge, MA (US)

(72) Inventors: Xuanhe Zhao, Allston, MA (US); Hyunwoo Yuk, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/085,692

(22) PCT Filed: Jun. 27, 2016

(86) PCT No.: PCT/US2016/039597
§ 371 (c)(1),
(2) Date: Sep. 17, 2018

(87) PCT Pub. No.: WO2017/164902
PCT Pub. Date: Sep. 28, 2017

(65) Prior Publication Data
US 2019/0070826 A1    Mar. 7, 2019

Related U.S. Application Data

(60) Provisional application No. 62/310,799, filed on Mar. 20, 2016.

(51) Int. Cl.
*A61L 27/52* (2006.01)
*A61L 31/12* (2006.01)
(Continued)

(52) U.S. Cl.
CPC ............... *B32B 3/30* (2013.01); *A61L 27/44* (2013.01); *A61L 27/52* (2013.01); *A61L 27/60* (2013.01);
(Continued)

(58) Field of Classification Search
CPC ........ A61L 27/52; A61L 31/12; A61L 31/145; B32B 3/20; B32B 7/04; B32B 7/10; B32B 25/04; B32B 25/14
See application file for complete search history.

(56) References Cited

U.S. PATENT DOCUMENTS 8,168,260 B2 *   5/2012   Limerkens ........... C08G 18/758
                                                          427/385.5
9,272,075 B2 *   3/2016   Antoni .................. A61L 29/085
(Continued)

FOREIGN PATENT DOCUMENTS

WO    1999019006 A1    4/1999
WO    2014169119 A1    10/2014

OTHER PUBLICATIONS

Yannas, I., Burke, J., Orgill, D. & Skrabut, E. Wound tissue can utilize a polymeric template to synthesize a functional extension of skin. Science 215, 174-176 (1952).
(Continued)

*Primary Examiner* — Joanna Pleszczynska
(74) *Attorney, Agent, or Firm* — Peter A. Nieves; Sheehan Phinney Bass & Green PA

(57) ABSTRACT

Hydrogel-elastomer hybrids with interfacial bonding tougher than epidermis-dermis interfaces and functional micro-channels and micro-patterns can be created by pre-shaping both elastomers and hydrogels before bonding to conserve their micro-structures, modifying cured elastomer surfaces with benzophenone for chemical bonding with hydrogels, and harnessing dissipative properties of tough hydrogels to achieve robust interfaces.

18 Claims, 29 Drawing Sheets

(51) Int. Cl.
  A61L 31/14    (2006.01)
  B32B 7/04     (2019.01)
  B32B 7/10     (2006.01)
  B32B 25/04    (2006.01)
  B32B 25/14    (2006.01)
  B32B 3/30     (2006.01)
  B32B 3/08     (2006.01)
  B32B 27/06    (2006.01)
  B32B 5/32     (2006.01)
  B32B 25/20    (2006.01)
  B32B 3/20     (2006.01)
  A61L 27/44    (2006.01)
  A61L 27/60    (2006.01)
  B32B 27/08    (2006.01)
  B32B 37/18    (2006.01)

(52) U.S. Cl.
  CPC ............ *A61L 31/12* (2013.01); *A61L 31/145* (2013.01); *B32B 3/08* (2013.01); *B32B 3/20* (2013.01); *B32B 5/32* (2013.01); *B32B 7/04* (2013.01); *B32B 7/10* (2013.01); *B32B 25/04* (2013.01); *B32B 25/042* (2013.01); *B32B 25/045* (2013.01); *B32B 25/14* (2013.01); *B32B 25/20* (2013.01); *B32B 27/06* (2013.01); *B32B 27/08* (2013.01); *B32B 37/182* (2013.01); *B32B 2250/03* (2013.01); *B32B 2255/102* (2013.01); *B32B 2255/26* (2013.01); *B32B 2307/402* (2013.01); *B32B 2307/50* (2013.01); *B32B 2307/51* (2013.01); *B32B 2307/54* (2013.01); *B32B 2307/546* (2013.01); *B32B 2307/7244* (2013.01); *B32B 2457/00* (2013.01); *B32B 2457/08* (2013.01); *B32B 2535/00* (2013.01)

(56) References Cited

U.S. PATENT DOCUMENTS

| | | | |
|---|---|---|---|
| 2010/0212824 | A1 | 8/2010 | Lionberger et al. |
| 2013/0149214 | A1 | 6/2013 | I Am et al. |
| 2014/0194547 | A1* | 7/2014 | Minagawa ............ C08F 291/00 522/115 |
| 2014/0373952 | A1 | 12/2014 | Vergne et al. |
| 2015/0038613 | A1 | 2/2015 | Sun et al. |
| 2015/0234204 | A1* | 8/2015 | Havenstrite ........ A61B 5/14532 351/159.33 |

OTHER PUBLICATIONS

Lee, K. Y. & Mooney, D. J. Hydrogels for tissue engineering. Chem. Rev. 101, 1869-1880 (2001).
Peppas, N. A., Hilt, J. Z., Khademhosseini, A. & Langer, R. Hydrogels in biology and medicine: From molecular principles to bionanotechnology. Adv. Mater. 18, 1345-1360 (2006).
Jeong, J.-W. et al. Wireless Optofluidic Systems for Programmable In Vivo Pharmacology and Optogenetics. Cell 162, 662-674 (2015).
Park, S. I. et al. Soft, stretchable, fully implantable miniaturized optoelectronic systems for wireless optogenetics, Nature biotechnology 33, 1280-1286 (2015).
Whitesides, G. M. The origins and the future of microfluidics. Nature 442, 368-373 (2006).
Casavant, B. P. et al. Suspend microfluidics. Proceedings of the National Academy of Sciences 110, 10111-10116 (2013).
Dong, L., Agarwal, A. K., Beebe, D. J. & Jiang, H. R. Adaptive liquid microlenses activated by stimuli-responsive hydrogels. Nature 442, 551-554 (2006).
Choi, M. et al. Light-guiding hydrogels for cell-based sensing and optogenetic synthesis in vivo. Natre photonics 7, 987-994 (2013).

Choi, M., Humar, M., Kim, S. & Yun, S. H. Step-Index Fiber Made of Biocompatible Hydrogels. Advanced Materials 27, 4081-4086 (2015).
Kim, D.-H. et al. Stretchable and foldable silicon integrated circuits. Science 320, 507-511 (2008).
Rogers, J.A., Someya, T. & Huang, Y. Materials and mechanics for stretchable electronics. Science 327, 1603-1607 (2010).
Xu, S. et al. Soft microfluidic assemblies of sensors, circuits, and radios for the skin. Science 344, 70-74 (2014), Tee, B. C.-K. et al. A skin-inspired organic digital mechanoreceptor. Science 350, 313-316 (2015).
Tee, B. C.-K. et al. A skin-inspired organic digital mechanoreceptor. Science 350, 313-316 (2015).
Shepherd, R. F. et al. Multigait soft robot. Proceedings of the National Academy of Sciences 108, 20400-20403 (2011).
Morin, S. A. et al. Camouflage and display for soft machines. Science 337, 828-832 (2012).
Keplinger, C. et al. Stretchable, transparent, ionic conductors, Science 341, 984-987 (2013).
Sun, J. Y., Keplinger, C., Whitesides, G. M. & Suo, Z. Ionic skin, Advanced Materials 26, 7608-7614 (2014).
Yang, C. H. et al. Ionic cable, Extreme Mechanics Letters 3, 59-65 (2015).
Lin, S. et al. Stretchable Hydrogel Electronics and Devices, Advanced Materials, (2015).
Casares, L. et al. Hydraulic fracture during epithelial stretching. Nat Mater 14, 343-351 (2015).
Wu, K. S., Stefik, M. M., Anathapadmanabhan, K. & Dauskardt, R. H. Graded delamination behavior of human stratum corneum. Biomaterials 27, 5861-5870 (2006).
Yuk, H., Zhang, T., Lin, S., Parada, G. A. & Zhao, X. Tough bonding of hydrogels to diverse non-porous surfaces, Nat Mater, 15, 190-196 (2016).
Dendukuri, D. et al. Modeling of oxygen-inhibited free radical photopolymerization in a PDMA microfluidic device, Macromolecules 41, 8547-8556 (2008).
Zhou, J., Ellis, A. V. & Voelcker, N. Recent developments in PDMS surface modification for microfluidic devices, Electrophoresis 31, 2-16 (2010).
Xia, Y. & Whitesiders, G. M. Soft lithography. Annual review of materials science 28, 153-184 (1998).
Wang, Y. et al. Covalent micropatterning of poly (dimethylsiloxane) by photografting through a mask. Analytical chemistry 77, 7539-7546 (2005).
Schneider, M. H., Tran, Y. & Tabeling, P. Benzophenone absorption and diffusion in poly(dimethylsiloxane) and its role in graft photopolymerization for surface modification. Langmuir 27, 1232-1240 (2011).
De Smet, N., Rymarczyk-Machal, M. & Schacht, E. Modification of polydimethylsiloxane surfaces using benzophenone, J Biomater Sci Polym Ed 20, 2039-2053 (2009).
Simmons, C. S., Ribeiro, A. J. & Pruitt, B. L. Formation of composite polyacrylamide and silicone substrates for independent control of stiffness and strain. Lab Chip 13, 646-649 (2013).
Yang, W. & Rånby, B. Radical living graft polymerization on the surface of polymeric materials. Macromolecules 29, 3308-3310 (1996).
Deng, J., Wang, L., Liu, L. & Yang, W. Developments and new applications of UV-induced surface graft polymerizations. Progress in Polymer Science 34, 156-193 (2009).
Dorman, G. & Prestwich, G. D. Benzophenone photophores in biochemistry. Biochemistry 33, 5661-5673 (1994).
Kawai, A., Hirakawa, M., Abe, T., Obi, K. Shibuya, K. Specific solvent effects on the structure and reaction dynamics of benzophenone ketyl radical. The Journal of Physical Chemistry A 105, 9628-9636 (2001).
Gong, J. P., Katsuyama, Y., Kurokawa, T. & Osada, Y. Double-network hydrogels with extremely high mechanical strength, Adv. Mater. 15, 1155-1158 (2003).
Gong, J. P. Why are double network hydrogels so tough? Soft Matter 6, 2583-2590 (2010).

(56) References Cited

OTHER PUBLICATIONS

Zhao, X. Multi-scale multi-mechanism design of tough hydrogels: Building dissipation into stretchy networks. Soft Matter 10, 672-687 (2014).
Sun, J.-Y. et al. Highly stretchable and tough hydrogels. Nature 489, 133-136 (2012).
Kendall, K. Thin-film peeling-the elastic term. J. Phys. D 8, 1449-1452 (1975).
Zhang, T., Lin, S., Yuk, H. & Zhao, X. Predicting fracture energies and crack-tip fields of soft tough materials. Extreme Mechanics Letters 4, 1-8 (2015).
Ogden, R. & Roxburgh, D. A pseudo-elastic model for the Mullins effect in filled rubber. Proc. R. Soc. Lond. Ser. A 455, 2861-2877 (1999).
Bai, Y. Transparent hydrogel with enhanced water retention capacity by introducing highly hydratable salt. Appl. Phys. Lett. 105, 151903 (2014).
Feinberg, A. W. et al. Muscular thin films for building actuators and powering devices. Science 317, 1366-1370 (2007).
Nawroth, J. C. et al. A tissue-engineered jellyfish with biomimetic propulsion. Nature biotechnology 30, 792-797 (2012).
Chen, A. Y., Zhong, C. & Lu, T. K. Engineering living functional materials. ACS synthetic biology 4, 8-11 (2015).

\* cited by examiner

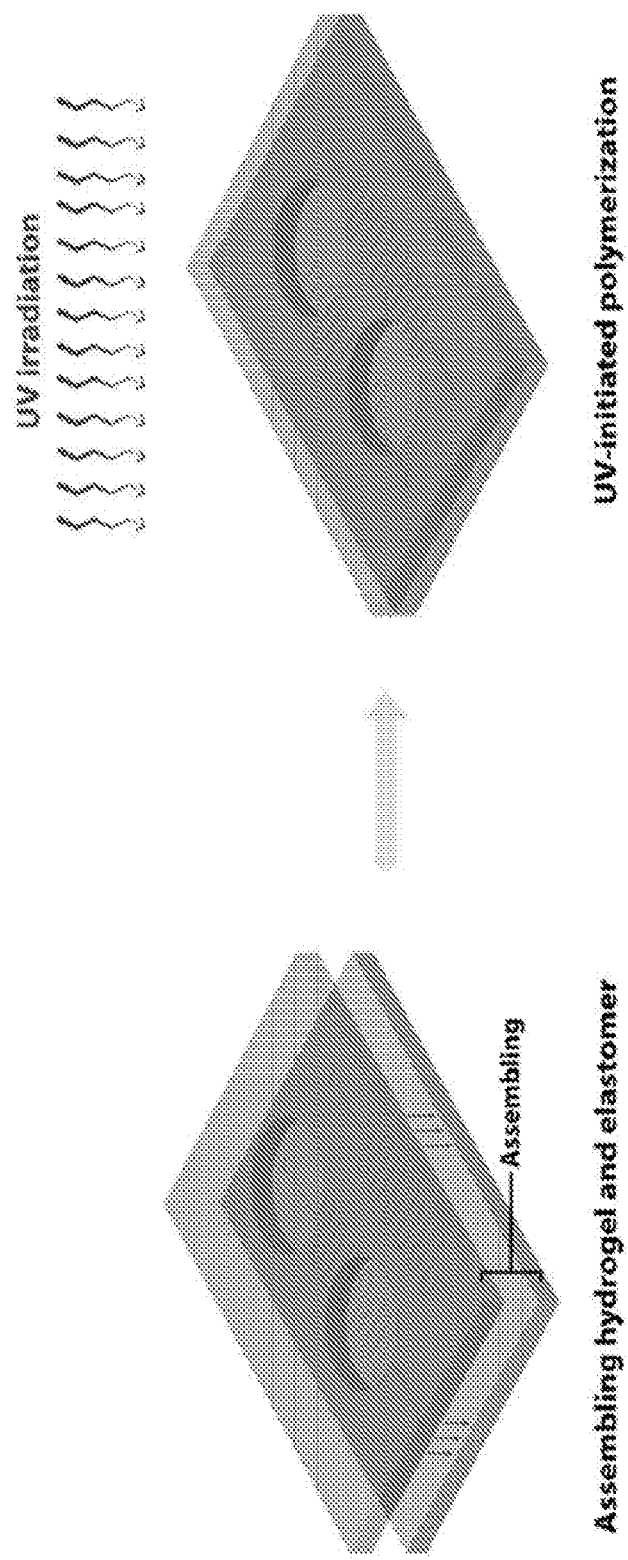

HYDROGEL-ELASTOMER HYBRIDS

CROSS-REFERENCE TO RELATED APPLICATIONS

This application is a national stage entry of International Application No. PCT/US2016/039597, filed Jun. 27, 2016, which claims the benefit of U.S. patent application Ser. No. 62/310,799, filed Mar 20, 2016. The contents of these prior applications are incorporated by reference herein in their entirety.

STATEMENT REGARDING FEDERALLY SPONSORED RESEARCH OR DEVELOPMENT

This invention was made with government support under Grant No. N00014-14-1-0528, awarded by the Office of Naval Research and Grant No. CMMI-1253495 the National Science Foundation. The government has certain rights in this invention.

TECHNICAL FIELD

This invention relates to a method of forming a tough hydrogel.

BACKGROUND

Soft materials including elastomers and hydrogels have enabled diverse modern technologies including tissue engineering, drug delivery, biomedical devices, microfluidics, optics, stretchable and bio-integrated electronics, and soft robotics. See, Yannas, I., Burke, J., Orgill, D. & Skrabut, E. Wound tissue can utilize a polymeric template to synthesize a functional extension of skin. *Science* 215, 174-176 (1982), Lee, K. Y. & Mooney, D. J. Hydrogels for tissue engineering. *Chem. Rev.* 101, 1869-1880 (2001), Peppas, N. A., Hilt, J. Z., Khademhosseini, A. & Langer, R. Hydrogels in biology and medicine: From molecular principles to bio-nanotechnology. *Adv. Mater.* 18, 1345-1360 (2006), Jeong, J.-W. et al. Wireless Optofluidic Systems for Programmable In Vivo Pharmacology and Optogenetics. *Cell* 162, 662-674 (2015), Park, S. I. et al. Soft, stretchable, fully implantable miniaturized optoelectronic systems for wireless optogenetics. *Nature biotechnology* 33, 1280-1286 (2015), Whitesides, G. M. The origins and the future of microfluidics. *Nature* 442, 368-373 (2006), Casavant, B. P. et al. Suspended microfluidics. *Proceedings of the National Academy of Sciences* 110, 10111-10116 (2013), Dong, L., Agarwal, A. K., Beebe, D. J. & Jiang, H. R. Adaptive liquid microlenses activated by stimuli-responsive hydrogels. *Nature* 442, 551-554 (2006), Choi, M. et al. Light-guiding hydrogels for cell-based sensing and optogenetic synthesis in vivo. *Nature photonics* 7, 987-994 (2013), Choi, M., Humar, M., Kim, S. & Yun, S. H. Step-Index Optical Fiber Made of Biocompatible Hydrogels. *Advanced Materials* 27, 4081-4086 (2015), Kim, D.-H. et al. Stretchable and foldable silicon integrated circuits. *Science* 320, 507-511 (2008), Rogers, J. A., Someya, T. & Huang, Y. Materials and mechanics for stretchable electronics. *Science* 327, 1603-1607 (2010), Xu, S. et al. Soft microfluidic assemblies of sensors, circuits, and radios for the skin. *Science* 344, 70-74 (2014), Tee, B. C.-K. et al. A skin-inspired organic digital mechanoreceptor. *Science* 350, 313-316 (2015), Shepherd, R. F. et al. Multigait soft robot. *Proceedings of the National Academy of Sciences* 108, 20400-20403 (2011), and Morin, S. A. et al. Camouflage and display for soft machines. *Science* 337, 828-832 (2012), each of which is incorporated by reference in its entirety. Both being mechanically compliant, elastomers have unique characters such as stability in various environments, mechanical robustness and easiness for micro-/nano-scale fabrications (e.g., soft lithography); whereas hydrogels' distinctive attributes include high water contents, permeability to various chemical and biological molecules, biocompatibility and/or biodegradability.

SUMMARY

A composition can include a first layer including a hydrogel and a second layer including an elastomer, wherein the first layer and the second layer are hybridized via covalent crosslinking. In certain embodiments, the composition can be included in a coating. In certain embodiments, such a coating can be included in a device or a sensor.

In certain embodiments, the second layer of the composition can be modified by a photoinitiator. In certain embodiments, the photoinitiator can be benzophenone.

In certain embodiments, the hydrogel can include a physically-crosslinked polymer network. In certain embodiments, the physically-crosslinked polymer network can include a polymer selected from a group consisting of alginate, hyaluronan, and chitosan.

In certain embodiments, the elastomer can include a chemically-crosslinked network. In certain embodiments, the chemically-crosslinked network can include a polymer selected from a group consisting of polyacrylamide, polyethylene glycol diacrylate, polydimethylacrylamide, poly (N-isopropylacrylamide), and poly (2-hydroxyethyl methacrylate).

In certain embodiments, the second layer can include microfluidic channels.

In certain embodiments, the composition can further include a third layer including an elastomer, where the first layer including a hydrogel is positioned between the second layer including an elastomer and the third layer including an elastomer. In certain embodiments, the elastomer of the third layer can be hybridized with the first layer via covalent crosslinking. In certain embodiments, the composition can further include a third layer including an electrical circuit pattern, wherein the third layer is positioned between the first layer and the second layer.

In certain embodiments, the first layer can include a conductive hydrogel.

A method of making a multi-layer structure can include forming a first layer including a hydrogel, forming a second layer including an elastomer, modifying the second layer with a photoinitiator, assembling the first layer and the second layer, and applying UV radiation.

In certain embodiments, the photoinitiator can be benzophenone.

In certain embodiments, forming a first layer can include forming a physically-crosslinked polymer network.

In certain embodiments, forming a second layer can include forming a chemically-crosslinked polymer network.

In certain embodiments, the physically-crosslinked polymer network can include a polymer selected from a group consisting of alginate, hyaluronan, and chitosan.

In certain embodiments, the chemically-crosslinked polymer network can include a polymer selected from a group consisting of polyacrylamide, polyethylene glycol diacrylate, polydimethylacrylamide, poly (N-isopropylacrylamide), and poly (2-hydroxyethyl methacrylate).

In certain embodiments, the method can further comprise including microfluidic channels in the second layer.

In certain embodiments, the method can further comprise forming a third layer including an elastomer such that the first layer including a hydrogel is positioned between the second layer including an elastomer and the third layer including an elastomer. In certain embodiments, forming a third layer can include hybridizing the first layer and the third layer via covalent crosslinking.

In certain embodiments, the method can further comprise including a third layer with an electrical circuit pattern, wherein the third layer is positioned between the first layer and the second layer.

In certain embodiments, the first layer can include a conductive hydrogel.

In certain embodiments, including a third layer with an electrical circuit pattern can include assembling the second layer and the third layer and adding a solution including a conductive hydrogel on top of the third layer.

Other aspects, embodiments, and features will be apparent from the following description, the drawings, and the claims.

BRIEF DESCRIPTION OF THE DRAWINGS

FIGS. 1A-1D show schematic illustration of the proposed method to create robust and microstructured hydrogel-elastomer hybrids.

FIG. 2A shows schematic illustration of the 90-degree peeling test on various hydrogel-elastomer hybrids. FIG. 2B shows photos of the hydrogel-elastomer interface during peeling test. FIG. 2C shows the measured peeling forces per width of the hydrogel sheets for various hydrogel-elastomer hybrids (in as-prepared state). FIG. 2D shows the calculated peeling forces per width of the hydrogel sheets for various hydrogel-elastomer hybrids in finite-element simulation. FIG. 2E shows summary of measured interfacial toughness of various hydrogel-elastomer hybrids using the proposed method at both as-prepared and fully-swollen states. Values represent mean and standard deviation of measured interfacial toughness for each elastomer materials (n=3-5).

FIG. 3A shows PAAm-alginate hydrogel bonded on Ecoflex® elastomer using the proposed method can withstand large deformation without debonding. FIG. 3B shows PAAm-alginate hydrogel bonded on Ecoflex® elastomer untreated by benzophenone detaches from the elastomer under small deformation due to weak adhesion.

FIG. 4A shows schematic illustration of the anti-dehydration elastomer coating for hydrogels. FIG. 4B shows the hydrogel-elastomer hybrid does not show noticeable change in its weight under ambient conditions (24° C. and 19% humidity) for 48 hours; whereas hydrogel without elastomer coating loses most of its water content after 48 hours. FIG. 4C shows snapshots of the hydrogel-elastomer hybrid and hydrogel during the dehydration experiments. The scale bars in c denote 10 mm.

FIG. 5A shows schematic illustration of the fabrication procedure for hydrogel-elastomer microfluidic chip. FIG. 5B shows the resultant hydrogel-elastomer microfluidic hybrid supports convection of chemicals (represented by food dye in different colors) in the microfluidic channels and diffusion of chemicals in the hydrogel. FIG. 5C shows the hydrogel-elastomer microfluidic hybrid can maintain functionality under large deformation (e.g., stretch ~2) without debonding failure or leakage thanks to the robust interfacial bonding.

FIG. 5D shows the hydrogel-elastomer microfluidic hybrid can be used as a platform for diffusion-reaction study. Acid (pH ~3) and base (pH ~10) solutions from two microfluidic channels diffuse in the pH-sensitive hydrogel and form regions of different colors (light red for acid and dark violet for base). The reaction of acid and base solutions in the hydrogel further form a neutral region (pH ~7, light green color). The scale bars in FIGS. 5B-5D denote 10 mm.

FIG. 6A shows schematic illustration of fabrication procedure for conductive hydrogel circuit patterned on flexible elastomer substrate. FIG. 6B shows ionically conductive PAAm-alginate hydrogel circuit bonded on an Ecoflex® elastomer substrate using the proposed method is robust under large deformation without visible failure. FIG. 6C shows the hydrogel circuit board connected with an AC power source can light up LED, and it can maintain its electrical functionality even under severe deformation. FIG. 6D shows a hydrogel circuit bonded on Ecoflex® elastomer without benzophenone treatment delaminates and fails under deformation, due to the weak hydrogel-elastomer bonding. The scale bars in FIGS. 6B-6D denote 10 mm.

FIG. 1A shows typical curves of peeling force per hydrogel width vs. displacement for various tough hydrogels bonded on PDMS substrates. FIG. 1B shows the measured interfacial toughness for various as-prepared tough hydrogels bonded on PDMS substrates. The values here represent mean and standard deviation of measured interfacial toughness for each tough hydrogel (n=3-5).

FIG. 11A shows photos of the peeling process of as-prepared PAAm-alginate tough hydrogel and PAAm common hydrogel physically-attached on PDMS substrates without benzophenone treatment on PDMS surfaces. FIG. 11B shows typical curves of peeling force per hydrogel width vs. displacement for as-prepared PAAm-alginate tough hydrogel and PAAm common hydrogel physically-attached on PDMS substrates. FIG. 11C shows the measured interfacial toughness for as-prepared PAAm-alginate tough hydrogel and PAAm common hydrogel physically-attached on PDMS substrates. The values here represent mean and standard deviation of measured interfacial toughness for each tough hydrogel (n=3-5).

DETAILED DESCRIPTION

Figure 1A:
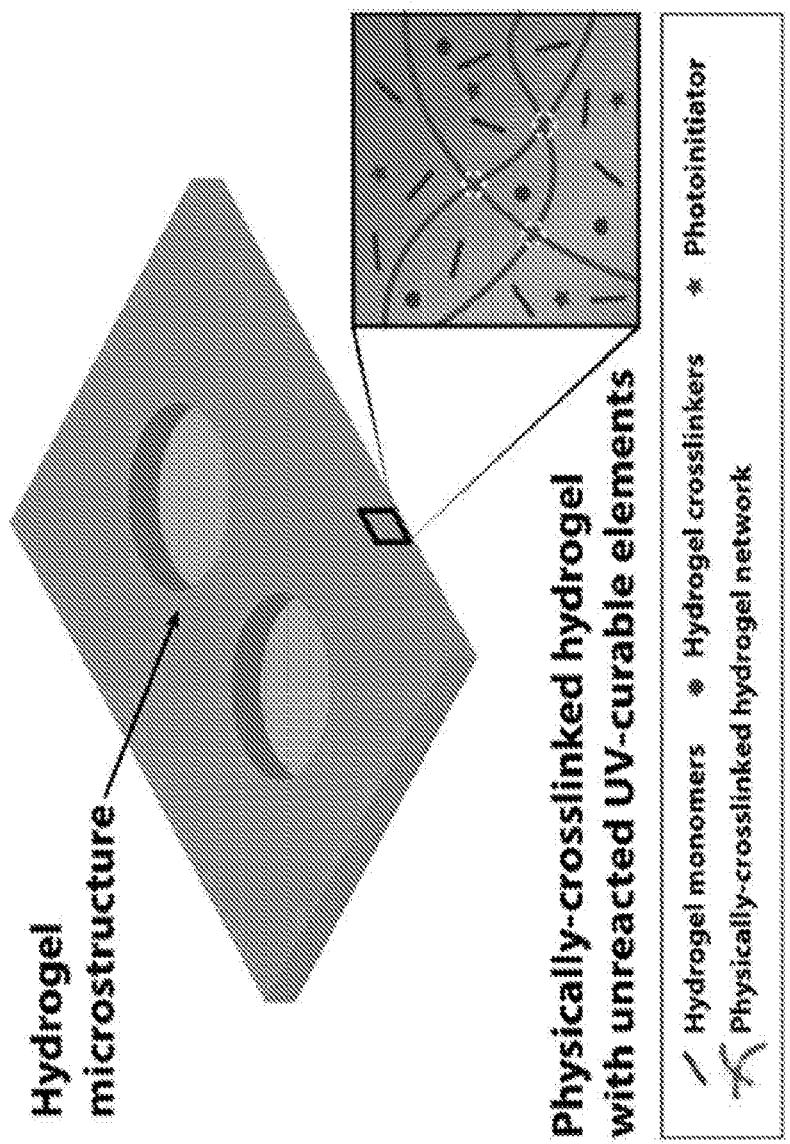

Human skin laminates elastomer-like epidermis and hydrogel-like dermis into a hybrid structure with robust interfaces (e.g., interfacial toughness over 100 Jm$^{-2}$) and functional microstructures (e.g., blood and lymphatic vessels). Soft hybrids that integrate the merits of elastomers and hydrogels have potential applications in areas as diverse as microfluidics, stretchable and bio-integrated electronics, soft robotics, tissue engineering, drug delivery and biomedical devices. However, existing hydrogel-elastomer hybrids suffer from limitations such as weak interfacial bonding, low robustness and difficulties in patterning microstructures.

Disclosed herein is a method of assembling hydrogels and elastomers into hybrids with extremely robust interfaces and functional microstructures. The shape and microstructure of tough hydrogel can be first set by physically crosslinking one polymer network in the hydrogel, and thereafter another polymer network in the hydrogel can be covalently anchored on elastomer surface modified by an initiator (e.g., a photoinitiator, such as, for example, benzophenone), leading to interfacial toughness over 1000 Jm$^{-2}$. The physically crosslinked hydrogel includes unreacted UV-curable elements so that the unreacted UV-curable elements can react with a region in the elastomer and form a direct linkage between the hydrogel and elastomer upon exposure to UV radiation. Here, the region in the elastomer that reacts with the unreacted UV-curable elements in the hydrogel is modified by the photoinitiator before forming a direct linkage between the hydrogel and the elastomer. In certain embodiments, microstructures such as micro-vessels and circuits can be included in the hydrogel-elastomer hybrids.

The method is generally applicable to various types of tough hydrogels and commonly-used elastomers including polydimethylsiloxane (PDMS) Sylgard® 184, polyurethane, latex, VHB™ and Ecoflex®. The robust and microstructured hydrogel-elastomer hybrids formed as such can be applied for anti-dehydration tough hydrogel with elastomer coating, stretchable and reactive hydrogel-elastomer microfluidics, and stretchable hydrogel circuit board patterned on elastomer.

Since the merits of elastomers and hydrogels are complementary to each other, it is desirable to integrate them into hybrid structures that can potentially transform their existing applications and enable new functions. See, Keplinger, C. et al. Stretchable, transparent, ionic conductors, *Science* 341, 984-987 (2013), Sun, J. Y., Keplinger, C., Whitesides, G. M. & Suo, Z. Ionic skin, *Advanced Materials* 26, 7608-7614 (2014), Yang, C. H. et al. Ionic cable, *Extreme Mechanics Letters* 3, 59-65 (2015), Lin, S. et al. Stretchable Hydrogel Electronics and Devices, *Advanced Materials*, (2015), and Casares, L. et al. Hydraulic fracture during epithelial stretching. *Nat Mater* 14, 343-351 (2015), each of which is incorporated by reference in its entirety. In nature, mammalian skins laminate elastomer-like epidermis and hydrogel-like dermis into hybrids with robust interfaces (e.g., interfacial toughness over 100 Jm$^{-2}$) and functional microstructures (e.g., blood and lymphatic vessels et al). See, Wu, K. S., Stefik, M. M., Ananthapadmanabhan, K. & Dauskardt, R. H. Graded delamination behavior of human stratum corneum. *Biomaterials* 27, 5861-5870 (2006), which is incorporated by reference in its entirety. However, elastomers and hydrogels in most technological applications are used separately, and few existing hydrogel-elastomer hybrids suffer from limitations such as weak interfacial bonding, low robustness and difficulties in patterning microstructures.

Tough bonding of hydrogels to rigid solids (e.g., glass, ceramics and metals) have been recently achieved by covalently crosslinking the stretchy polymer networks of tough hydrogels on surfaces of the solids. See, Yuk, H., Zhang, T., Lin, S., Parada, G. A. & Zhao, X. Tough bonding of hydrogels to diverse non-porous surfaces, *Nat Mater,* 15, 190-196 (2016), which is incorporated by reference in its entirety. However, this method is generally inapplicable in forming hydrogel-elastomer hybrids with robust interfaces and functional microstructures, mainly due to three challenges: i.) Elastomers are highly permeable to oxygen that leads to the oxygen inhibition effect by which the free-radical polymerization or surface covalent crosslinking of hydrogel polymers are seriously hampered. See, Dendukuri, D. et al. Modeling of oxygen-inhibited free radical photopolymerization in a PDMS microfluidic device, *Macromolecules* 41, 8547-8556 (2008), which is incorporated by reference in its entirety. ii.) Aging or hydrophobic recovery of functionalized elastomer surfaces also significantly lower the effectiveness of hydrogel bonding on elastomers. See, Zhou, J., Ellis, A. V. & Voelcker, N. H. Recent developments in PDMS surface modification for microfluidic devices. *Electrophoresis* 31, 2-16 (2010), which is incorporated by reference in its entirety. iii.) Most elastomers and hydrogels are fabricated by curing pre-elastomer resins and pre-gel solutions, and thus the pre-gel solutions (or pre-elastomer resins) can infiltrate into microstructures patterned on cured elastomers (or hydrogels) to diminish microstructures such as micro-channels. See, Xia, Y. & Whitesides, G. M. Soft lithography. *Annual review of materials science* 28, 153-184 (1998), which is incorporated by reference in its entirety. A general method capable of fabricating hydrogel-elastomer hybrids with robust interfaces and functional microstructures is still a critical demand and central challenge in the field.

Inspired by the structures and functions of mammalian skin, a general method capable of assembling pre-shaped elastomers and hydrogels into hybrids with extremely robust interfaces (e.g., interfacial toughness over 1000 Jm$^{-2}$) and functional microstructures (e.g., micro-channels and circuit patterns) is developed. This method addresses the above-mentioned challenges by integrating three innovations in fabrication of soft materials and hybrids: i.) physical crosslinking of dissipative polymer networks in tough hydrogels to set their shapes and microstructures; ii.) modification of cured elastomer surfaces with benzophenone to alleviate oxygen inhibition effect and activate elastomer surfaces for hydrogel polymer grafting; and iii.) covalent crosslinking of stretchy polymer networks in pre-shaped hydrogels to elastomers to give extremely robust and microstructured interfaces. The method is generally applicable to various types of commonly-used elastomers including polydimethylsiloxane (PDMS) Sylgard® 184, polyurethane, latex, VHB™ and Ecoflex® and diverse tough hydrogels including PAAm-algiante, PAAm-hyaluronan, PAAm-chitosan, PEGDA-alginate and PEGDA-hyaluronan (Note: PAAm stands for polyacrylamide, PEGDA stands for polyethylene glycol diacrylate). See, Lin, S. et al. Stretchable Hydrogel Electronics and Devices, *Advanced Materials*, (2015), which is incorporated by reference in its entirety. A number of novel applications can take advantage of the robust and microstructured hydrogel-elastomer hybrids including anti-dehydration tough hydrogel with elastomer coating, stretchable diffusive and reactive hydrogel-elastomer microfluidics, and stretchable hydrogel circuit board patterned on elastomer. This disclosure not only addresses the long-lasting challenge of robust hydrogel-elastomer integration but also makes new applications in various fields possible by introducing a new way to harness distinctive yet complementary advantages of hydrogels and elastomers.

Some embodiments can be particularly advantageous due to the biocompatible nature of hydrogels. Hydrogels are particularly resistant to biological fouling. For example, the hydrogel-elastomer hybrids can be included in a coating for a device or a sensor used in vitro. In such a case, biological entities (e.g., endothelial cells, proteins, etc.) may adhere to the coating and may result in failure of the device or the sensor. Because hydrogels can be resistant to biological fouling, such disadvantages can be mitigated.

In certain embodiments, a hydrogel layer can be positioned between two elastomer layers so that the dehydration if the hydrogel is effectively prevented.

In certain embodiments, an elastomer layer of the hydrogel-elastomer hybrids can include microfluidic channels so that the resultant hydrogel-elastomer microfluidic hybrids can maintain functionality under large deformation without debonding failure or leakage.

In certain embodiments, a film with circuit pattern can be positioned between a conductive hydrogel layer and an elastomer layer so that the resultant hydrogel circuit board can maintain its electrical functionality even under severe deformation.

Robust bulk hydrogel coating on elastomeric medical devices (e.g., catheter or contraceptive devices) can provide very slippery and biofunctional (e.g., drug release) surface robustly integrated on top of any types of existing elastomeric medical devices. Also, bulk hydrogel layer hybrid with elastomeric structure can provide versatile containment for living materials such as bacteria or mammalian cells. For instance, hydrogel layer can act as leakage barrier for genetically engineered living materials while allowing exchange of nutrients, oxygen, waste and functional biomolecules from/toward living materials. These potential advantages will provide greater flexibility and opportunities in adopting living materials in various conventional elastomer-based applications by simply integrating another layers of biofunctional hydrogels.

As used herein, the term "hydrogel" is given its ordinary meaning in the art and refers to a material comprising a polymer network that is able to trap and contain water. The hydrogel may include polymer chains that are crosslinked, either directly or via a crosslinking agent. In certain embodiments, the hydrogel can form a physically-crosslinked network. In certain embodiments, the hydrogel can form a chemically-crosslinked network. The degree of crosslinking may be varied, in some cases, to tailor the extent to which the gel absorbs or retains fluids. In certain embodiments, the hydrogel can be an elastic synthetic hydrogel. Examples of polymers capable of forming hydrogels include but not limited to, collagen, silicon-containing polymers, polyacrylamides, crosslinked polymers (e.g., polyethylene oxide, polyAMPS and polyvinylpyrrolidone), polyvinyl alcohol, acrylate polymers (e.g., sodium polyacrylate), and copolymers with an abundance of hydrophilic groups.

As used herein, the term "elastomer" is given its ordinary meaning in the art and refers to a material comprising a polymer with elasticity. Each of the monomers which link to form an elastomer is usually made of carbon, hydrogen, oxygen or silicon. Elastomers are amorphous polymers existing above their glass transition temperature, so that considerable segmental motion is possible, thus relatively soft and deformable. The covalent cross-linkages ensure that the elastomer can be highly stretchable when a stress is applied on it and will return to its original configuration when the stress is removed. Examples of polymers with elastomeric properties include polydimethylsiloxane (PDMS) Sylgard® 184, polyurethane, latex, VHB™ and Ecoflex®.

As used herein, the term "initiator" is given its ordinary meaning in the art and refers to a molecule that creates reactive species (free radicals, cations or anions) when exposed to radiation (x-ray, UV or visible) or heat. The initiator can be a photoinitiator, for example, benzophenone, benzoin ethyl ether, benzoin isobutyl ether, benzoin methyl ether, 4,4'-bis(diethylamino)benzophenone and 4,4'-Bis(dimethylamino)benzophenone. In other embodiments, the initiator can be a thermal initiator, for example, t-butylperoxide, cumyl peroxyneodecanoate and cumyl peroxyneoheptanoate. See, for example, Wang, Y. et al. Covalent micropatterning of poly (dimethylsiloxane) by photografting through a mask. *Analytical chemistry* 77, 7539-7546 (2005), and Schneider, M. H., Tran, Y. & Tabeling, P. Benzophenone absorption and diffusion in poly (dimethylsiloxane) and its role in graft photo-polymerization for surface modification. *Langmuir* 27, 1232-1240 (2011), each of which is incorporated by reference in its entirety.

The initiator described herein can chemically bind two layers. The initiator also can scavenge oxygen.

The benzophenone can be used as a photoinitiator for polymeric materials. See, De Smet, N., Rymarczyk-Machal, M. & Schacht, E. Modification of polydimethylsiloxane surfaces using benzophenone. *J Biomater Sci Polym* Ed 20, 2039-2053 (2009), Simmons, C. S., Ribeiro, A. J. & Pruitt, B. L. Formation of composite polyacrylamide and silicone substrates for independent control of stiffness and strain. *Lab Chip* 13, 646-649 (2013), Yang, W. & Ranby, B. Radical living graft polymerization on the surface of polymeric materials. *Macromolecules* 29, 3308-3310 (1996), Deng, J., Wang, L., Liu, L. & Yang, W. Developments and new applications of UV-induced surface graft polymerizations. *Progress in Polymer Science* 34, 156-193 (2009), Dorman, G. & Prestwich, G. D. Benzophenone photophores in biochemistry. *Biochemistry* 33, 5661-5673 (1994), and Kawai, A., Hirakawa, M., Abe, T., Obi, K. & Shibuya, K. Specific solvent effects on the structure and reaction dynamics of benzophenone ketyl radical. *The Journal of Physical Chemistry A* 105, 9628-9636 (2001), each of which is incorporated by reference in its entirety.

The following table shows tough hydrogels can be synthesized based on multiple combinations of different stretchy polymer networks and dissipative polymer networks. Each combination can give a tough hydrogel which can be form robust hybrids with various elastomers following the proposed method. The following table shows examples of stretchy polymer networks and dissipative polymer networks that can be used for such combinations and some specific non-limiting embodiments using those combinations of materials.

|  |  | Stretchy polymer networks (as UV-curable elements) | | | | |
| --- | --- | --- | --- | --- | --- | --- |
|  |  | Polyacrylamide (AAm) | Polyethylene glycol diacrylate (PEGDA) | Polydimethyl acrylamide (DMAA) | Poly (N-isopropylacrylamide) (NIPAM) | Poly (2-hydroxyethyl methacrylate) (HEMA) |
| Physically-crosslinked dissipative polymer networks | Alginate | 12 wt. % AAm, 0.017 wt. % MBAA, 2 wt. % alginate, CaSO$_4$ (20 mM concentration in gel) | 20 wt. % PEGDA, 2.5 wt. % alginate, CaSO$_4$ (20 mM concentration in gel) | 12 wt. % DMAA, 2 wt. % alginate, CaSO$_4$ (20 mM concentration in gel) | 12 wt. % NIPAM, 0.017 wt. % MBAA, 2 wt. % alginate, CaSO$_4$ (20 mM concentration in gel) | 12 wt. % HEMA, 0.017 wt. % MBAA, 2 wt. % alginate, CaSO$_4$ (20 mM concentration in gel) |
|  | Hyaluronan (HA) | 18 wt. % AAm, 0.026 wt. % MBAA, 2 wt. % HA, Iron (III) chloride (3 mM concentration in gel) | 20 wt. % PEGDA, 2 wt. % HA, Iron (III) chloride (3 mM concentration in gel) | 18 wt. % DMAA, 2 wt. % HA, Iron (III) chloride (3 mM concentration in gel) | 18 wt. % NIPMA, 0.026 wt. % MBAA, 2 wt. % HA, Iron (III) chloride (3 mM concentration in gel) | 18 wt. % HEMA, 0.026 wt. % MBAA, 2 wt. % HA, Iron (III) chloride (3 mM concentration in gel) |
|  | Chitosan | 24 wt. % AAm, 0.034 wt. % MBAA, 2 wt. % chitosan, Tripolyphosphate (3 mM concentration in gel) | 20 wt. % PEGDA, 2 wt. % Chitosan, Tripolyphosphate (3 mM concentration in gel) | 24 wt. % DMAA, 2 wt. % chitosan, Tripolyphosphate (3 mM concentration in gel) | 24 wt. % NIPAM, 0.034 wt. % MBAA, 2 wt. % chitosan, Tripolyphosphate (3 mM concentration in gel) | 24 wt. % HEMA, 0.034 wt. % MBAA, 2 wt. % chitosan, Tripolyphosphate (3 mM concentration in gel) |

Fabrication of Hydrogel-Elastomer Hybrids.

Although hydrogels and elastomers have been widely used in diverse technologies, they still cannot be integrated into hybrid structures with robust interfaces and functional microstructures, mainly due to challenges including elastomer surfaces' inhibition of polymer crosslinking and grafting, and fluidic characters of pre-gel solutions and/or pre-elastomer resins that diminish interfacial microstructures during hybrid formation.

Figure 1B:
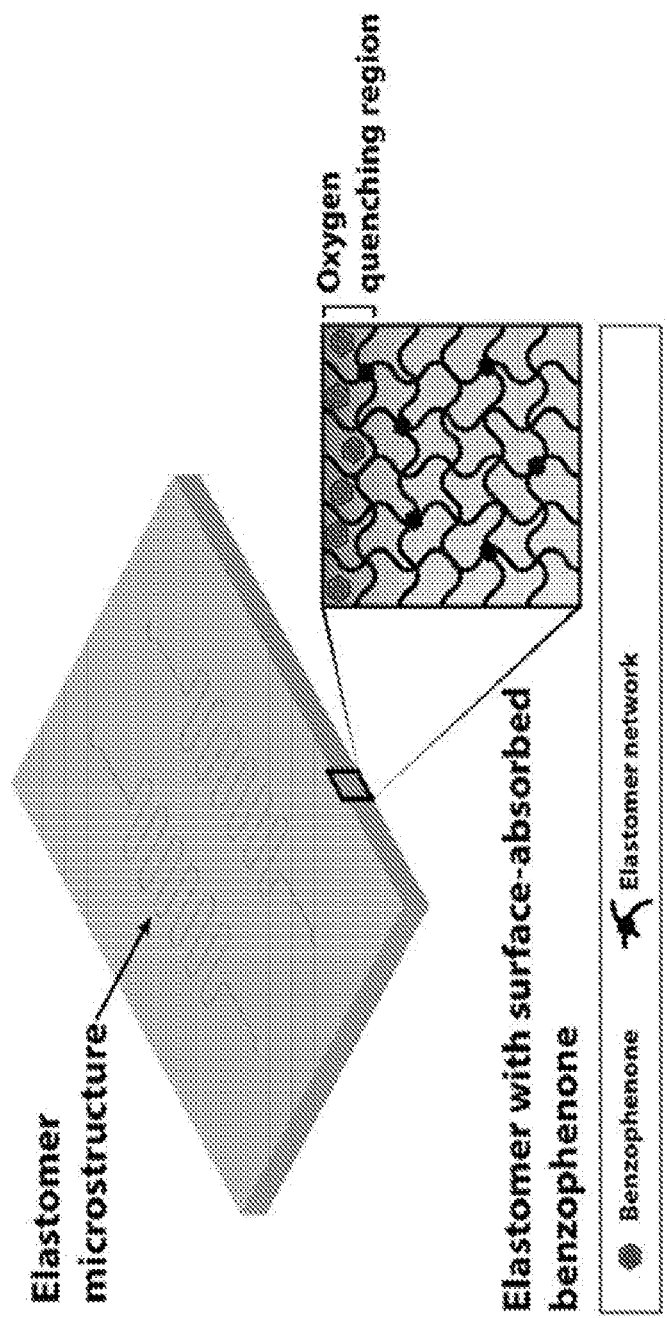
Figure 1D:
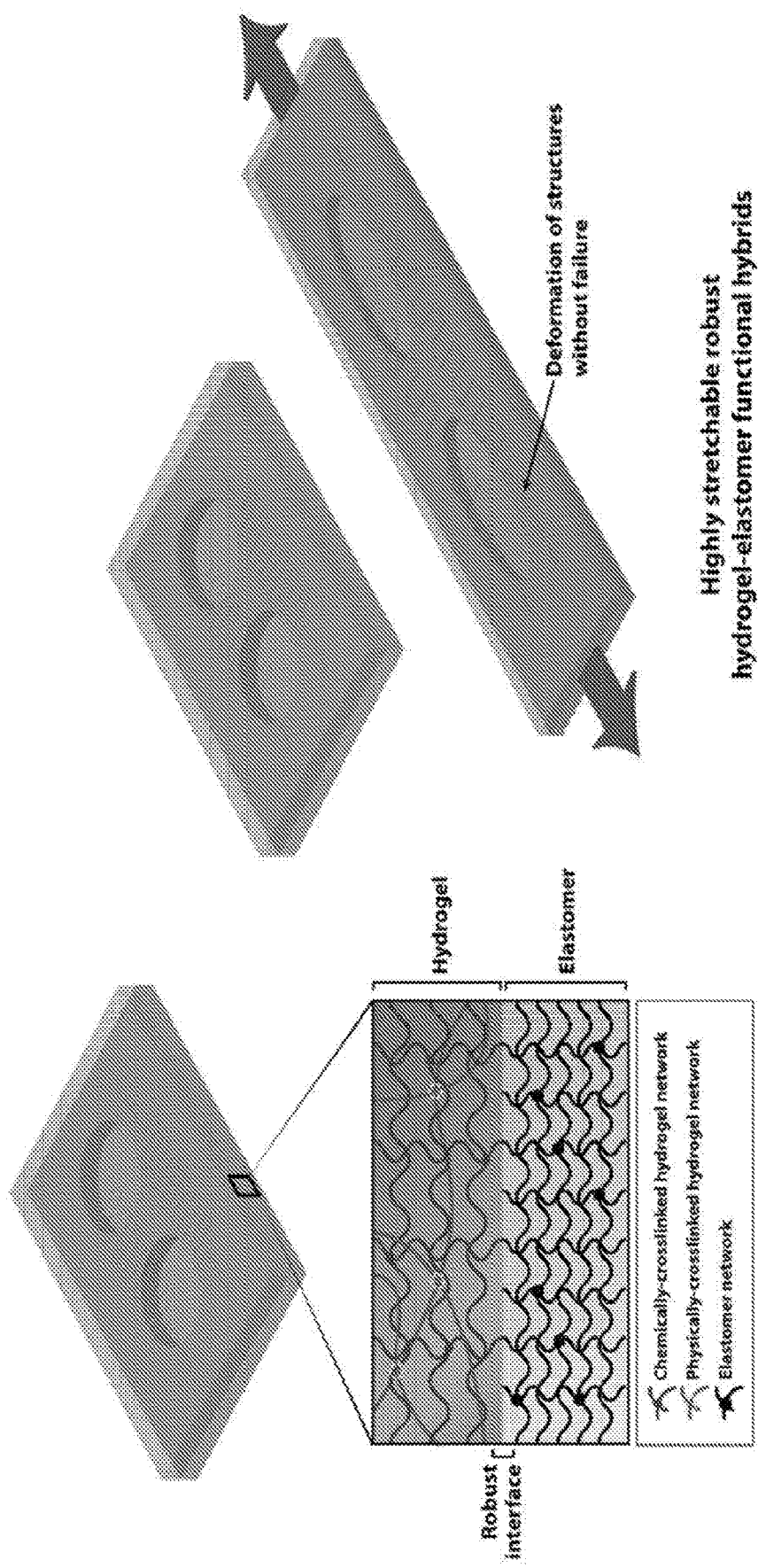

To address these challenges, a simple yet versatile method is developed to assemble pre-shaped elastomers and hydrogels into hybrids with robust interfaces and functional microstructures (FIGS. 1A, 1B, and 1C). The hybrids can be formed by bonding tough hydrogels of interpenetrating polymer networks with elastomers (FIG. 1A). One polymer network of the hydrogel is first physically-crosslinked, while infiltrated with monomer/macromonomer solution of the other polymer network. The physical crosslinking sets the shape and microstructures of the hydrogel. In one embodiment, the surface of a cured elastomer with patterned microstructures can be treated with a photoinitiator, for example, with benzophenone (FIG. 1B). The pre-shaped hydrogel and elastomer are assembled together followed by UV irradiation to chemically crosslink the other polymer network in the hydrogel (FIG. 1C). After UV irradiation, the resultant hydrogel-elastomer hybrid forms extremely robust interfaces due to the covalently anchored polymer network in the hydrogel on elastomer surface (FIG. 1D). The pre-patterned microstructures in elastomers and hydrogels are also preserved in the hybrid. The hybrids can be highly stretched without interfacial failure.

The essential ideas of the method are briefly described as follows (see EXAMPLES for detailed procedure). Robust hydrogel-elastomer interfaces first require high toughness of the constituent hydrogels. Tough hydrogels generally consist of stretchy polymer networks and other components that dissipate mechanical energy under deformation. See, Gong, J. P., Katsuyama, Y., Kurokawa, T. & Osada, Y. Double-network hydrogels with extremely high mechanical strength. *Adv. Mater.* 15, 1155-1158 (2003), Gong, J. P. Why are double network hydrogels so tough? *Soft Matter* 6, 2583-2590 (2010), Zhao, X. Multi-scale multi-mechanism design of tough hydrogels: Building dissipation into stretchy networks. *Soft Matter* 10, 672-687 (2014), and Sun, J.-Y. et al. Highly stretchable and tough hydrogels. *Nature* 489, 133-136 (2012), each of which is incorporated by reference in its entirety.

Figure 7:
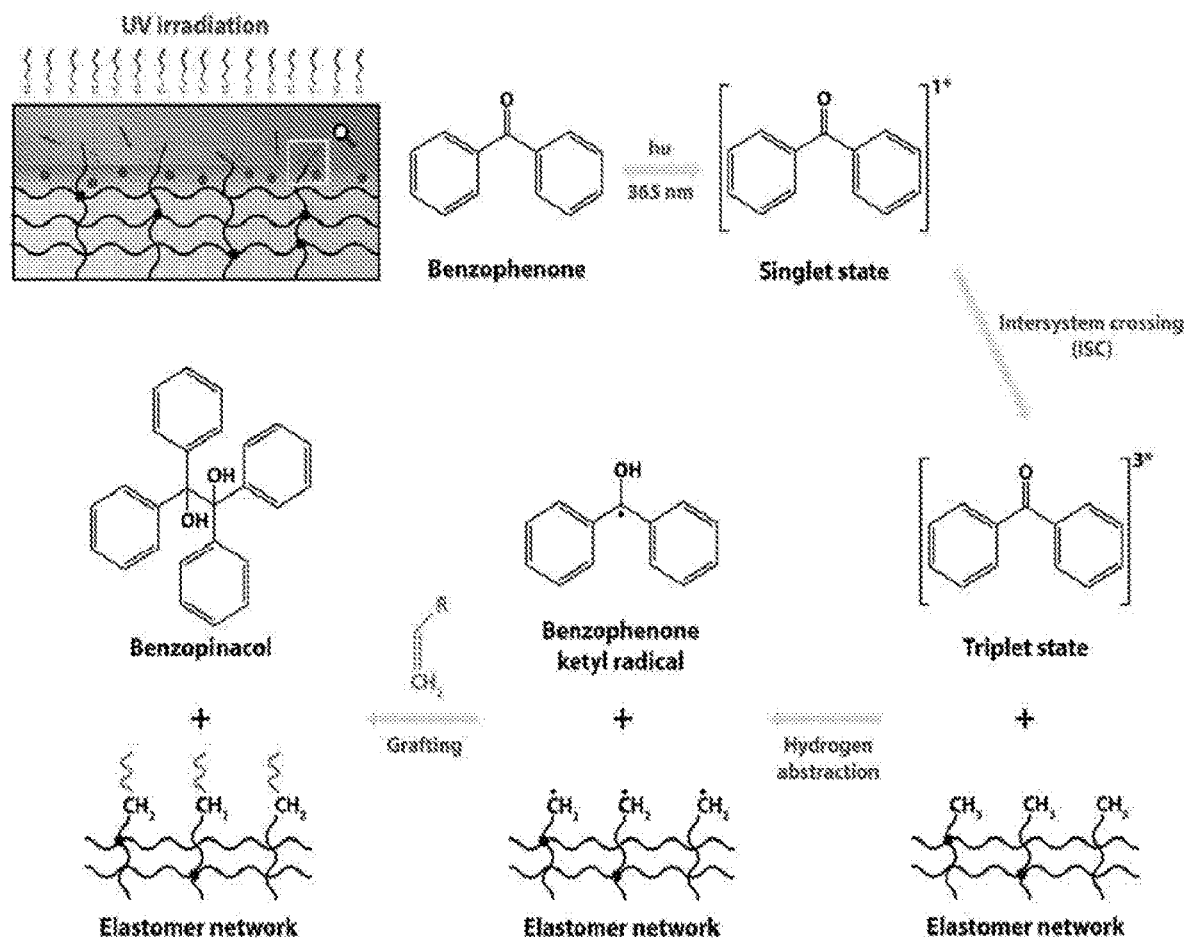
FIG. 7 shows schematics of benzophenone chemistry for hydrogel bonding.

The method disclosed herein utilizes physically-crosslinked dissipative polymer networks and covalently-crosslinked stretchy polymer networks to form tough hydrogels. In one embodiment, first, the dissipative network is physically crosslinked to form a hydrogel infiltrated with monomer/macromonomer solution of the stretchy network, which can be crosslinked in future steps (FIG. 1A). The physical crosslinking allows the hydrogel to maintain its pre-designed shapes and microstructures during assembly with elastomers. Similarly, the elastomer is also cured with pre-determined shapes and microstructures prior to bonding with hydrogels. In order to address elastomers' oxygen inhibition effect, elastomer surfaces were treated with benzophenone via swelling-driven surface absorption of benzophenone solution (FIG. 1B). The benzophenone can also act as an UV-assisted grafting agent for covalently cross-linking hydrogel polymers on elastomer surfaces (FIG. 7). Under UV irradiation, surface absorbed benzophenone is excited into a singlet state which is followed by conversion into a triplet state through intersystem crossing. The triplet-state benzophenone consecutively changes into benzophenone ketyl radical by abstracting a hydrogen from surrounding unreactive C—H bonds in elastomer polymer. Then benzophenone ketyl radical mediates the grafting of stretchy polymer networks of the hydrogel onto the reactive sites on the elastomer surface, generating benzopinacol as a final reaction product.

Thereafter, the pre-shaped hydrogel and elastomer are assembled into a hybrid, and then the stretchy polymer network in the hydrogel is crosslinked and grafted on the surface of elastomer—leading to robust and microstructured interfaces capable of large deformation and high stretchability (FIGS. 1C and 1D). Furthermore, since the proposed method does not rely on specific types of polymers, it is widely applicable to various commonly-used elastomers including PDMS Sylgard® 184, polyurethane, latex, VHB™ and Ecoflex® and tough hydrogels including PAAm-algiante, PAAm-hyaluronan, PAAm-chitosan, PEGDA-alginate and PEGDA-hyaluronan.

Robustness of Hydrogel-Elastomer Hybrids.

Figure 2A:
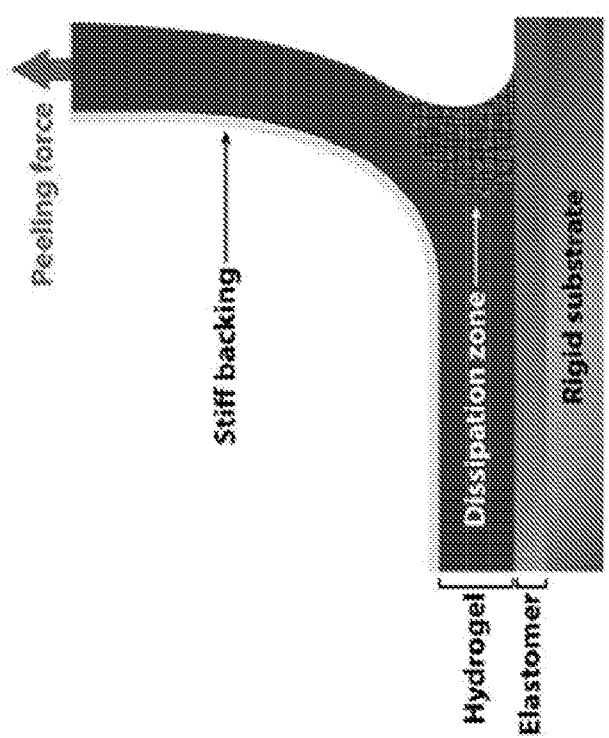
FIGS. 2A-2E show experiment and simulation results of 90-degree peeling tests on hydrogel-elastomer hybrids.

To quantify the robustness of hydrogel-elastomer hybrids fabricated with the proposed method, the standard 90-degree peeling test was used to measure interfacial toughness of hydrogel sheets (thickness, 3 mm) bonded on elastomer substrates (thickness, 1 mm) as illustrated FIG. 2A (see EXAMPLES for details). The bottom surface of elastomer is constrained on a thick rigid plate during the peeling test; while the top surface of the hydrogel is attached to a thin stiff backing (polyethylene terephthalate film of ~70 μm thickness), which prevents the hydrogel's elongation along the peeling direction. See, Kendall, K. Thin-film peeling—the elastic term. *J. Phys. D* 8, 1449-1452 (1975), which is incorporated by reference in its entirety. Therefore, the measured steady-state peeling force per unit width of the hydrogel sheet gives the interfacial toughness of the hybrid.

Figure 2B:
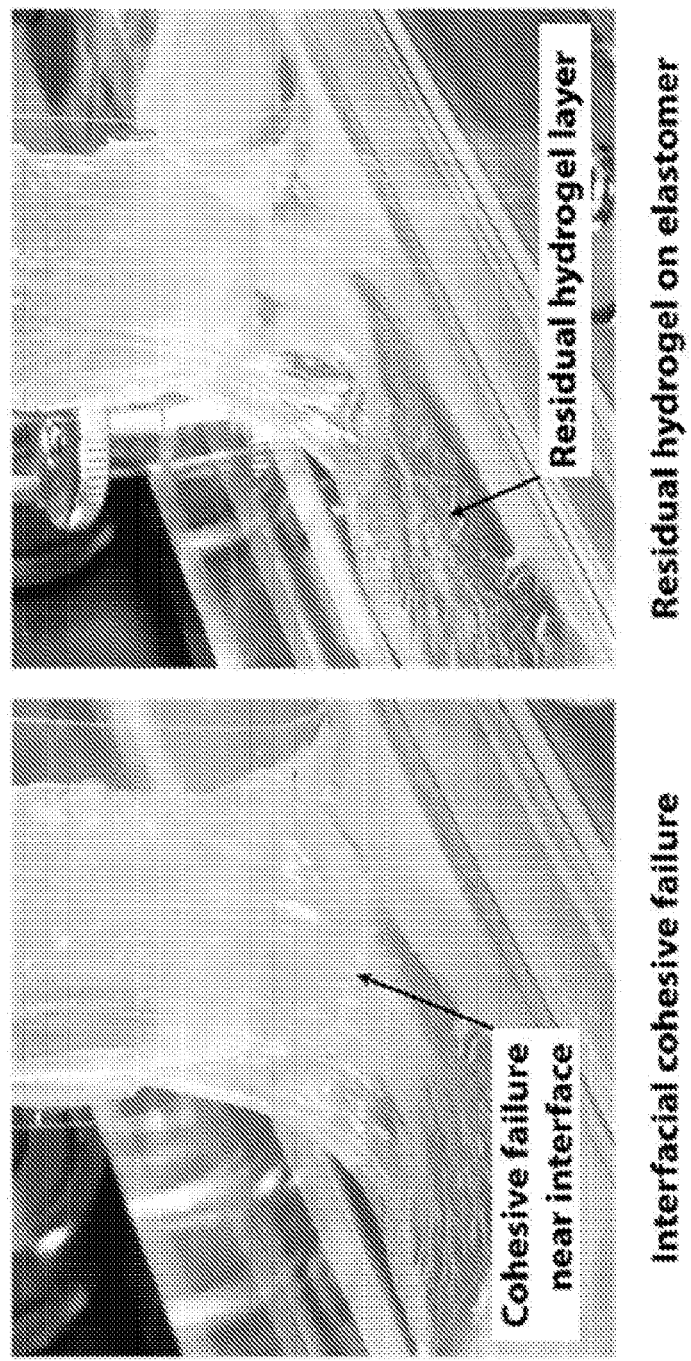
Figures 2C, 2D:
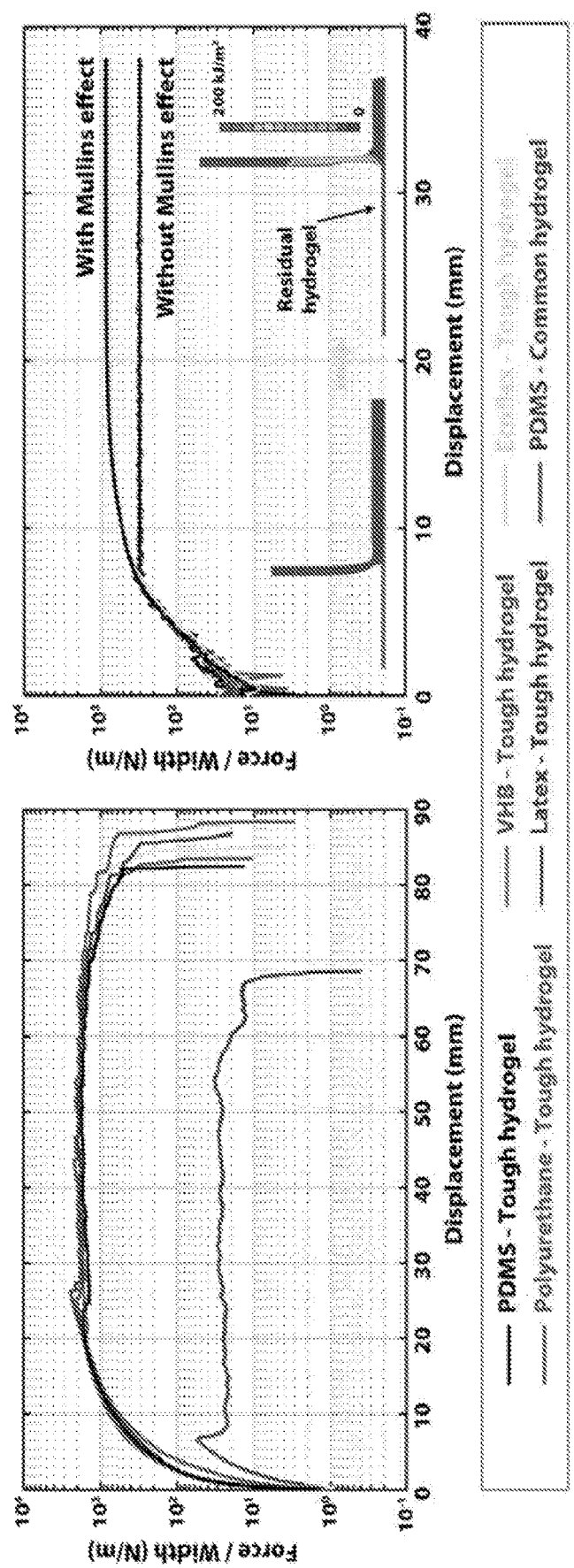
Figure 2E:
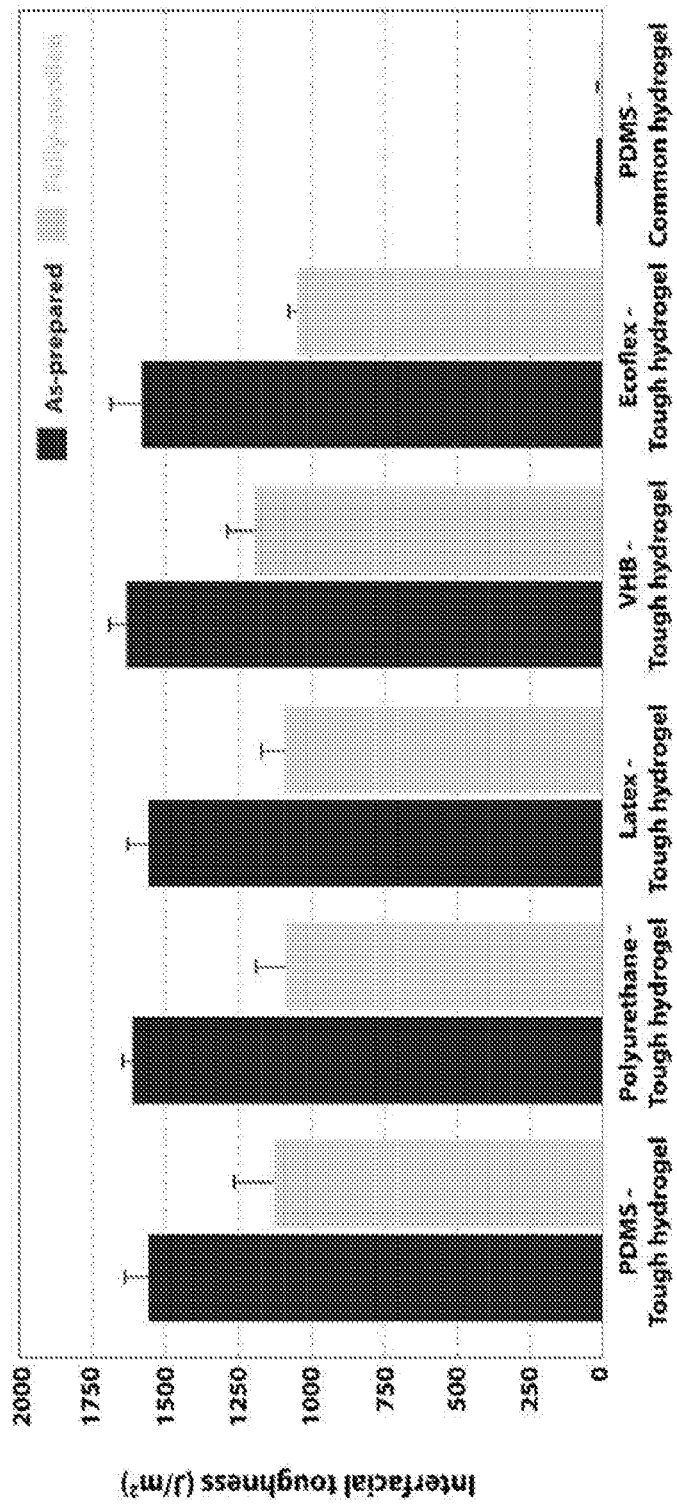
Figure 10A:
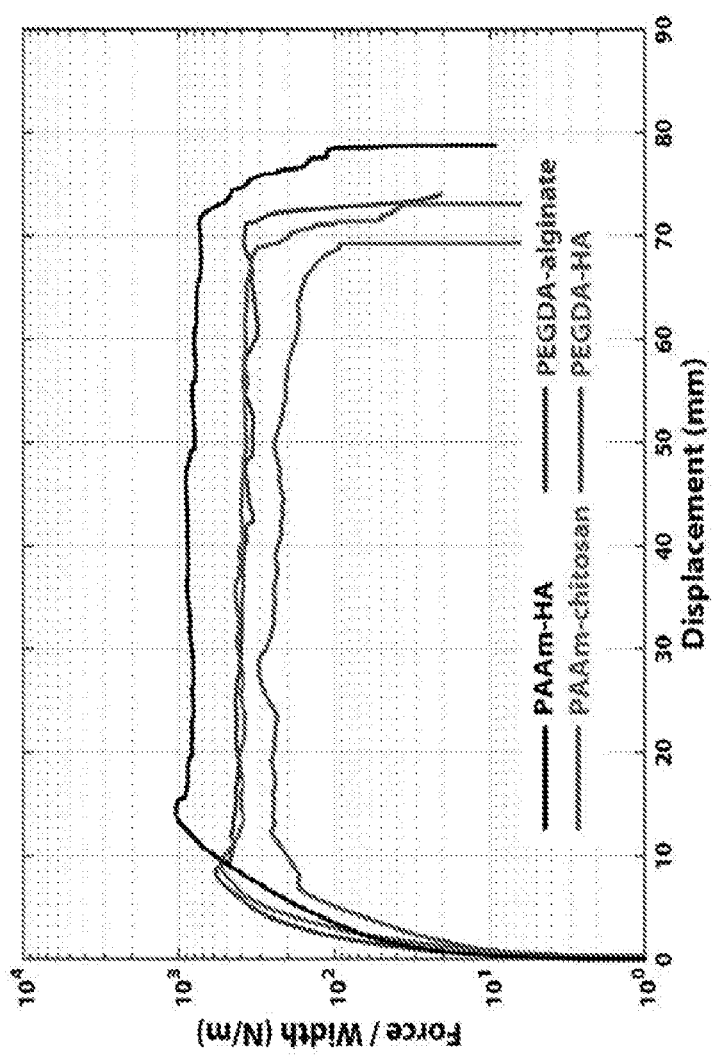
FIGS. 10A-10B show interfacial toughness of various as-prepared tough hydrogels bonded on PDMS substrates.
Figure 10B:
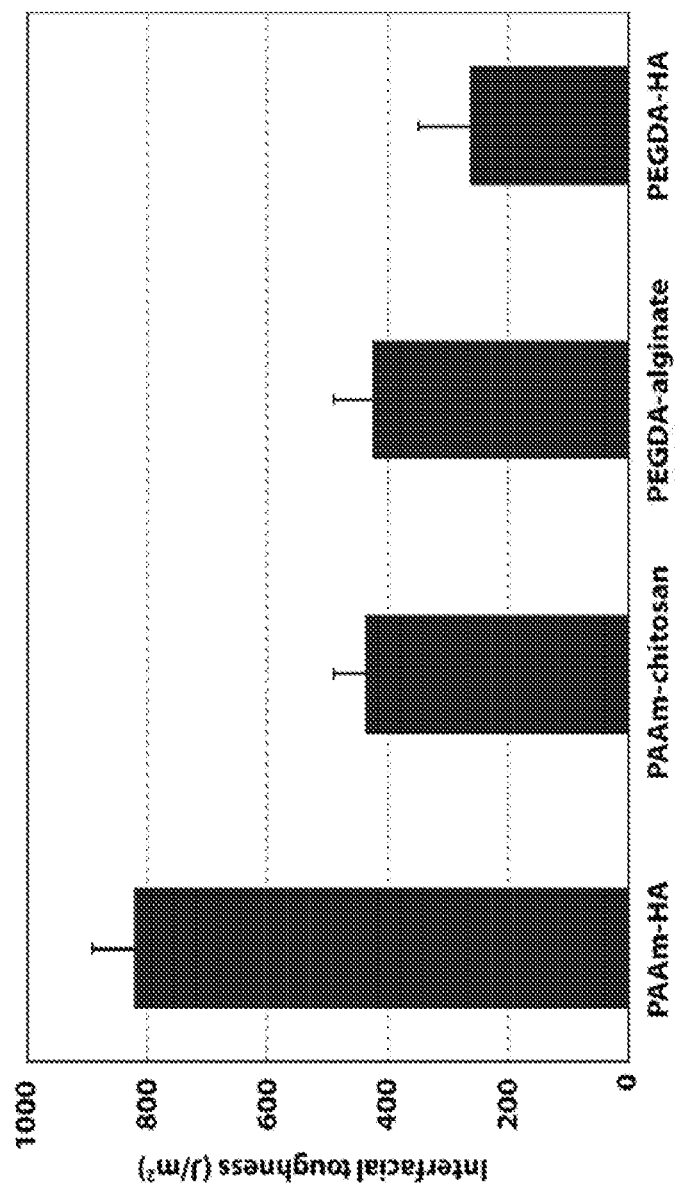

As shown in FIGS. 2C and 2E, the proposed method is indeed capable of achieving consistently high interfacial toughness for PAAm-alginate tough hydrogels (in as-prepared state) bonded onto various elastomers including PDMS Sylgard® 184 (1560 $Jm^{-2}$), polyurethane (1610 $Jm^{-2}$), latex (1520 $Jm^{-2}$), VHB™ (1630 $Jm^{-2}$) and Ecoflex® (1580 $Jm^{-2}$). It is noted that the measured interfacial toughness for PAAm-alginate hydrogel on different elastomers are very similar to one other (FIGS. 2C and 2E). This similarity can be explained by the images of the hydrogel-elastomer interface during peeling test (FIG. 2B). It can be seen that the tough hydrogel, instead of the hydrogel-elastomer interface, undergoes a cohesive failure near the interface during the peeling test, leaving a residual layer of hydrogel (~0.2 mm thickness) on the elastomer substrates. Since the elastomer substrates have insignificant effect on cohesive failure of hydrogels, the measured values for different elastomer substrates are similar. This observation further demonstrates the robust bonding between hydrogels and elastomers achieved with the proposed method, as the crack propagates through the tough hydrogel instead of the interface. In addition, as shown in FIGS. 10A-10B, the proposed method can also enable robust bonding between various other tough hydrogels including PAAm-hyaluronan (821 $Jm^{-2}$), PAAm-chitosan (436 $Jm^{-2}$), PEGDA-alginate (427 $Jm^{-2}$) and PEGDA-hyaluronan (262 $Jm^{-2}$) and elastomers (e.g., PDMS Sylgard® 184), demonstrating the versatility of the proposed method.

Figure 9:
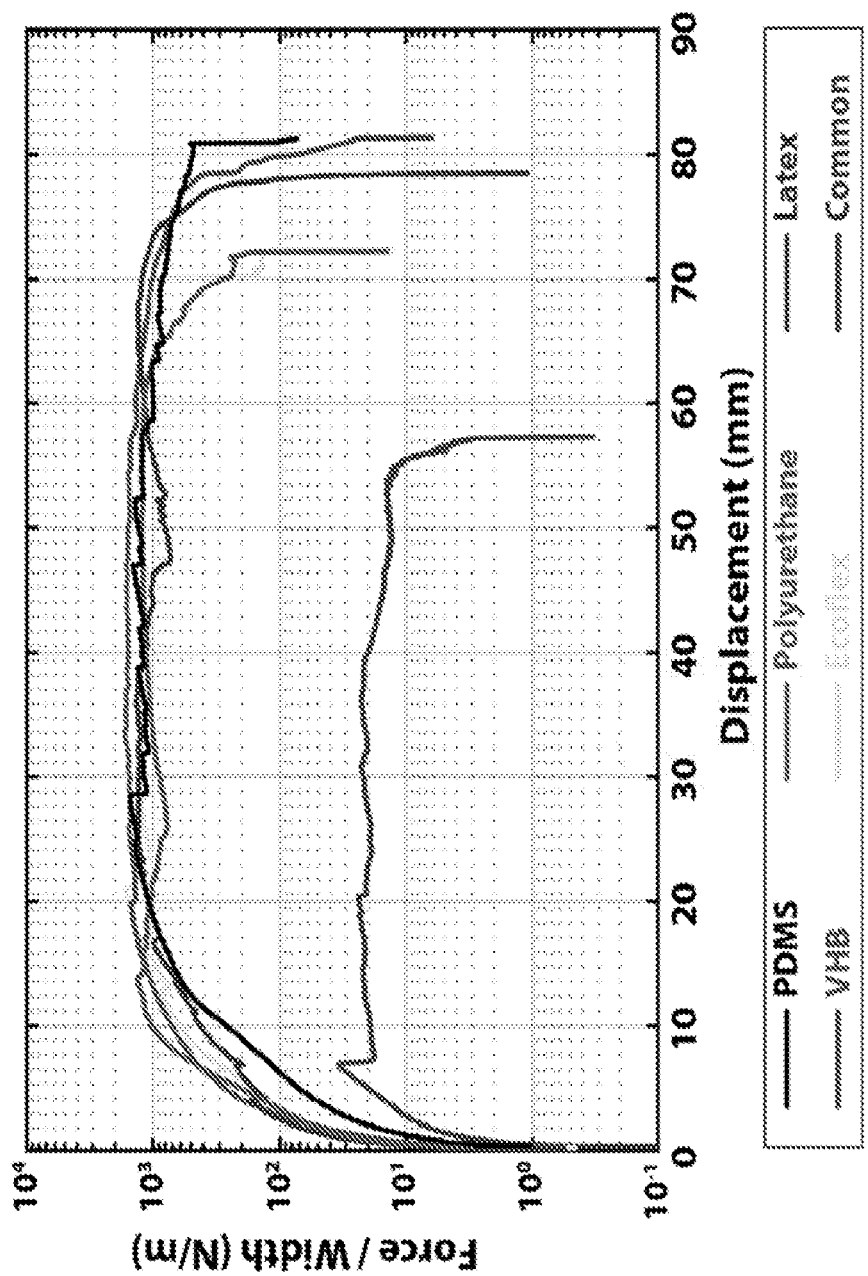
FIG. 9 shows the curves of peeling force per width of hydrogel sheet vs. displacement for various types of hydrogel-elastomer hybrids at fully-swollen state.

Since hydrogel-elastomer hybrids can be used in wet environments, the 90-degee peeling test was carried out on fully-swollen hydrogel-elastomer hybrids by immersing them in deionized water for over 24 hours until they reach equilibrium swollen state. As shown in FIGS. 2E and 9, The measured interfacial toughness of the fully-swollen samples are still consistently high and similar to one another, i.e., PDMS Sylgard® 184 (1131 $Jm^{-2}$), polyurethane (1087 $Jm^{-2}$), latex (1092 $Jm^{-2}$), VHB™ (1191 $Jm^{-2}$) and Ecoflex® (1044 $Jm^{-2}$), owning to cohesive failure of the hydrogel during the peeling test. Note that curves labeled as PDMS, polyurethane, latex, VHB™ and Ecoflex® are based on fully-swollen PAAm-alginate hydrogel bonded on these elastomers; while the curve labeled as Common is based on fully-swollen PAAm hydrogel bonded on PDMS. These results demonstrate that the interfaces of hydrogel-elastomer hybrids prepared with the proposed method are robust in both as-prepared and swollen states.

To validate that high toughness of the hydrogel is critical to achieving robust hydrogel-elastomer interface, a common PAAm hydrogel with similar shear moduli as the PAAm-alginate hydrogel (~30 kPa) was bonded on elastomer substrate using a similar method (see Materials and Methods for details). While cohesive failure also occurs in the PAAm hydrogels during peeling test, the measured interfacial toughness is 24 $Jm^{-2}$ and 21 $Jm^{-2}$ for as-prepared and fully-swollen samples, respectively—much lower than the values for PAAm-alginate tough hydrogels due to the low fracture toughness of PAAm hydrogels (FIG. 2E). See, Yuk, H., Zhang, T., Lin, S., Parada, G. A. & Zhao, X. Tough bonding of hydrogels to diverse non-porous surfaces. *Nat Mater*, 15, 190-196 (2016), which is incorporated by reference in its entirety. These results validate that the dissipative properties and high toughness of the hydrogels is critical to achieving robust hydrogel-elastomer hybrids.

Figure 11A:
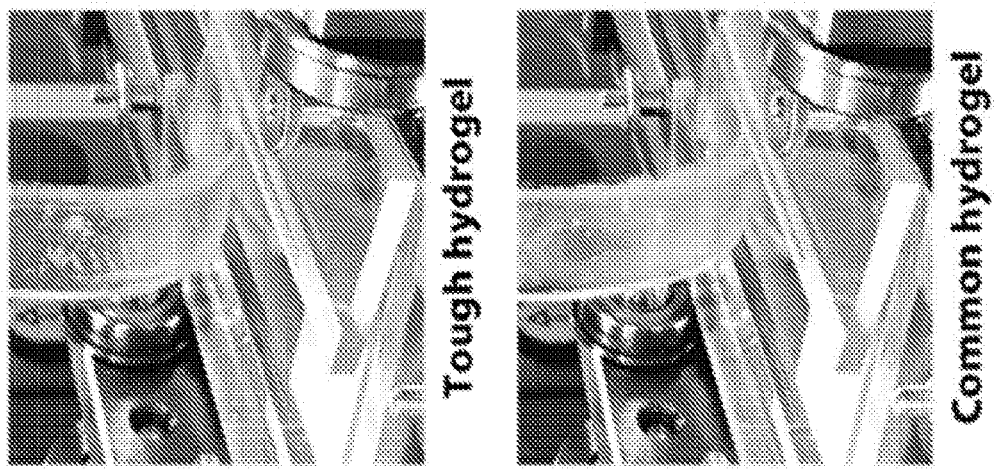
FIGS. 11A-11C show the 90-degree peeling test of hydrogels bonded on untreated elastomer substrates.
Figure 11B:
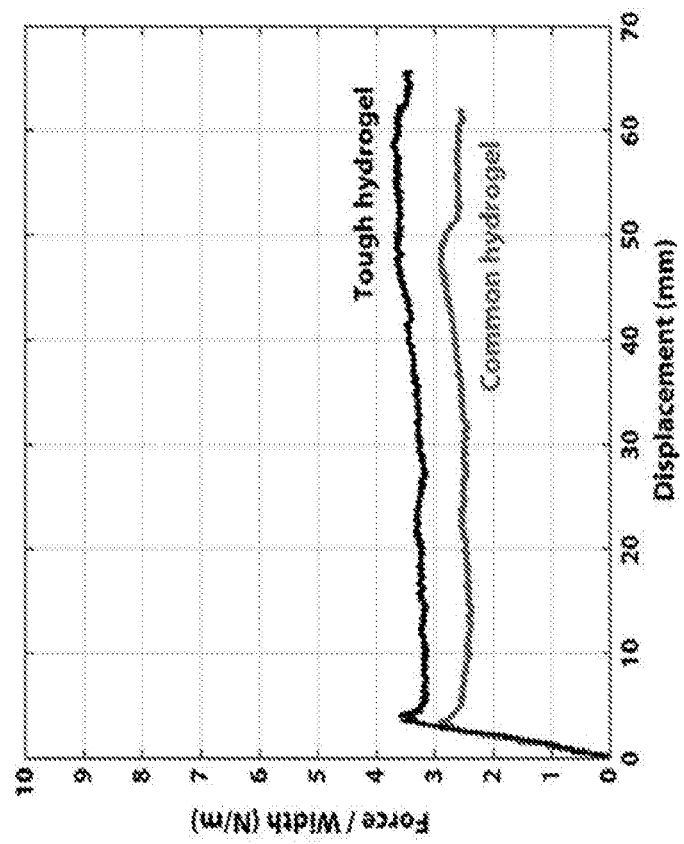
Figure 11C:
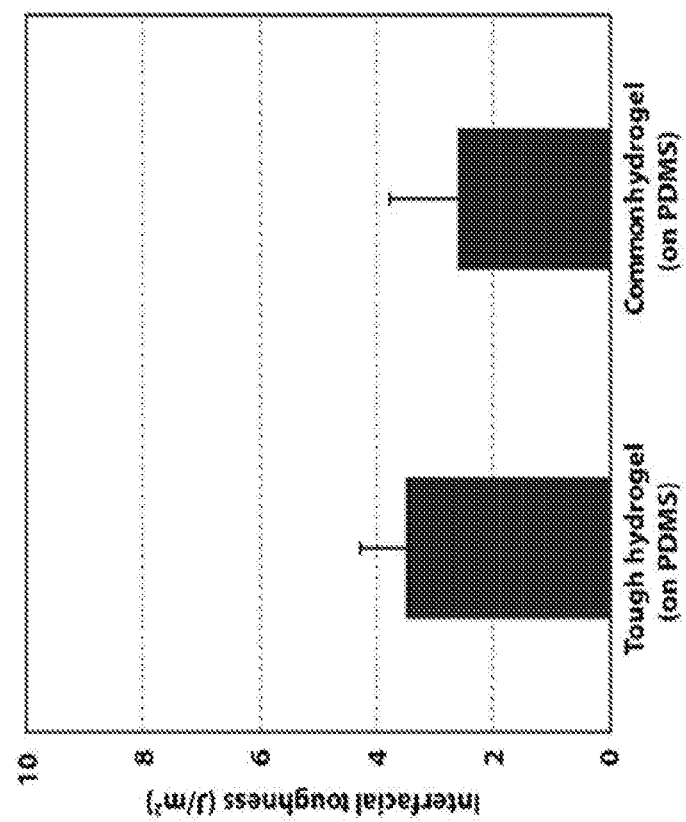

To study the effects of benzophenone treatment of elastomer surfaces on hydrogel-elastomer interfaces, common PAAm hydrogel and tough PAAm-alginate hydrogel was bonded on elastomer substrates untreated by benzophenone. From FIG. 11A, it can be seen that the failure occurs at the hydrogel-elastomer interfaces and the measured interfacial toughness is very low, 2.6 $Jm^{-2}$ and 3.5 $Jm^{-2}$ for PAAm and PAAm-alginate hydrogels, respectively (FIGS. 11B and 11C). These results indicate that the untreated elastomer surfaces indeed hamper the grafting and crosslinking of acrylamide to the surface, leading to very weak hydrogel-elastomer interfaces.

Figure 13:
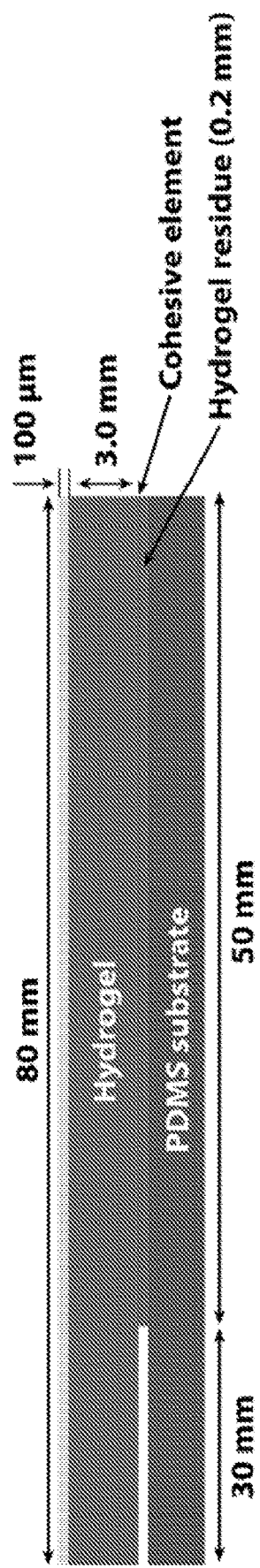
FIG. 13 shows schematic illustration of the finite-element model for numerical simulation of peeling.
Figure 14:
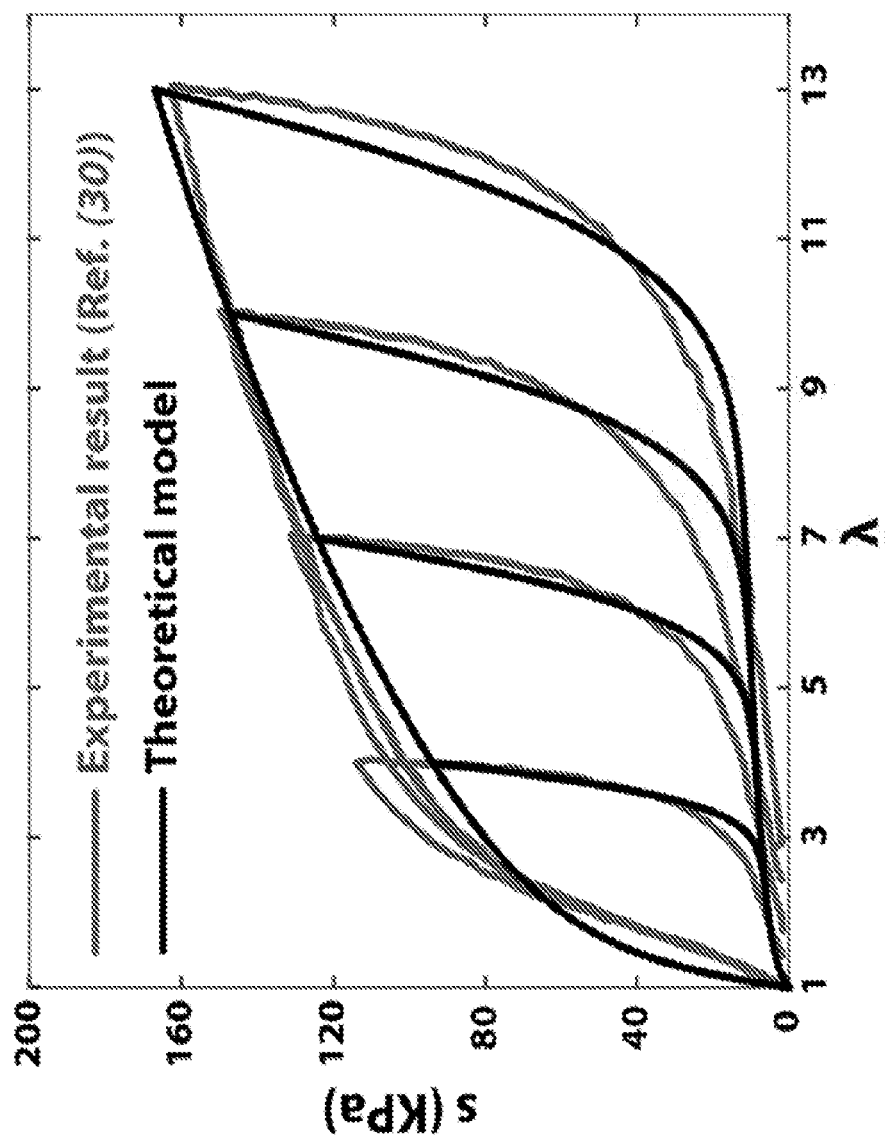
FIG. 14 shows stress-strain hysteresis of the PAAm-alginate hydrogel measured from the previous reported experimental data and fitted with the Mullins effect model.

To quantitatively understand the measured interfacial toughness of hydrogel-elastomer hybrids using the proposed method, a finite-element model was used to simulate the 90-degree peeling experiment on hydrogel-elastomer hybrids (FIG. 2D). See EXAMPLES and FIG. 13 for details of the model. See also Yuk, H., Zhang, T., Lin, S., Parada, G. A. & Zhao, X. Tough bonding of hydrogels to diverse non-porous surfaces. *Nat Mater*, 15, 190-196 (2016), and Zhang, T., Lin, S., Yuk, H. & Zhao, X. Predicting fracture energies and crack-tip fields of soft tough materials. *Extreme Mechanics Letters* 4, 1-8 (2015), each of which is incorporated by reference in its entirety. Following experimental observations, it is assumed that the hydrogel undergoes cohesive failure in the simulation of peeling tests, leaving a residual layer of hydrogel with thickness of 0.2 mm on the elastomer substrate. The interface between the residual layer and the other part of the hydrogel is characterized as a layer of cohesive elements that prescribe the intrinsic fracture energy of the hydrogel. See, Zhang, T., Lin, S., Yuk, H. & Zhao, X. Predicting fracture energies and crack-tip fields of soft tough materials. *Extreme Mechanics Letters* 4, 1-8 (2015), which is incorporated by reference in its entirety. The mechanical properties of the tough hydrogel are prescribed by the Ogden model with parameters obtained from mechanical tests on the PAAm-alginate hydrogel (FIG. 14).

See, Sun, J.-Y. et al. Highly stretchable and tough hydrogels. *Nature* 489, 133-136 (2012), and Ogden, R. & Roxburgh, D. A pseudo-elastic model for the Mullins effect in filled rubber. *Proc. R. Soc. Lond. Ser. A* 455, 2861-2877 (1999), each of which is incorporated by reference in its entirety. The dissipative properties of the hydrogels are characterized by Mullins effect. See, Yuk, H., Zhang, T., Lin, S., Parada, G. A. & Zhao, X. Tough bonding of hydrogels to diverse non-porous surfaces. *Nat Mater,* 15, 190-196 (2016), and Zhang, T., Lin, S., Yuk, H. & Zhao, X. Predicting fracture energies and crack-tip fields of soft tough materials. *Extreme Mechanics Letters* 4, 1-8 (2015), each of which is incorporated by reference in its entirety. From FIG. 2D, it can be seen that different elastomer substrates indeed have negligible effect on the calculated interfacial toughness of the hybrids, due to cohesive failure of the hydrogels. On the other hand, the simulated interfacial toughness is significantly decreased if dissipative properties are eliminated (i.e., without Mullins effect) in the hydrogel while maintaining other parameters the same, validating the importance of dissipative properties of the hydrogels in achieving robust interfaces. FIG. 2D inset pictures are snapshots of the 90-degree peeling simulation. The contours indicate the energy dissipation per unit area in the material.

Figure 3A:
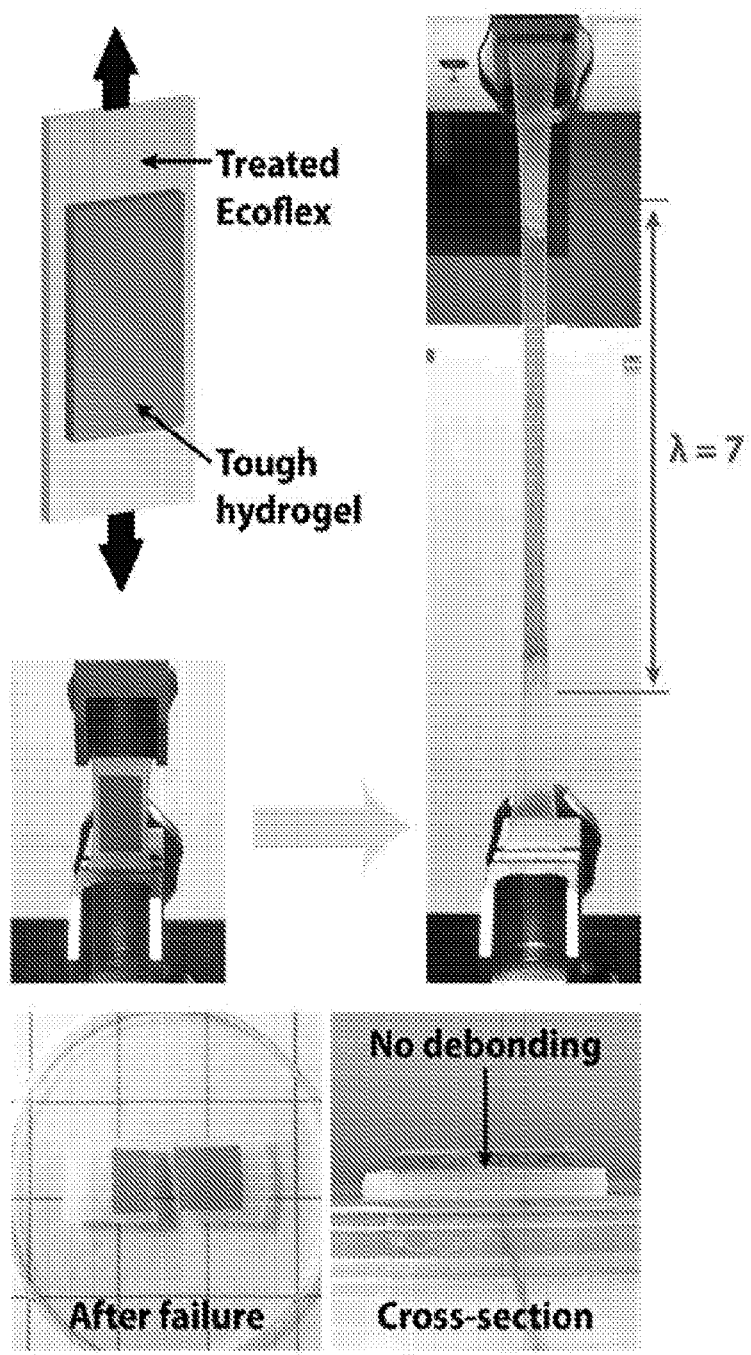
FIG. 3A-3B show hydrogel-elastomer hybrids under high stretches.
Figure 3B:
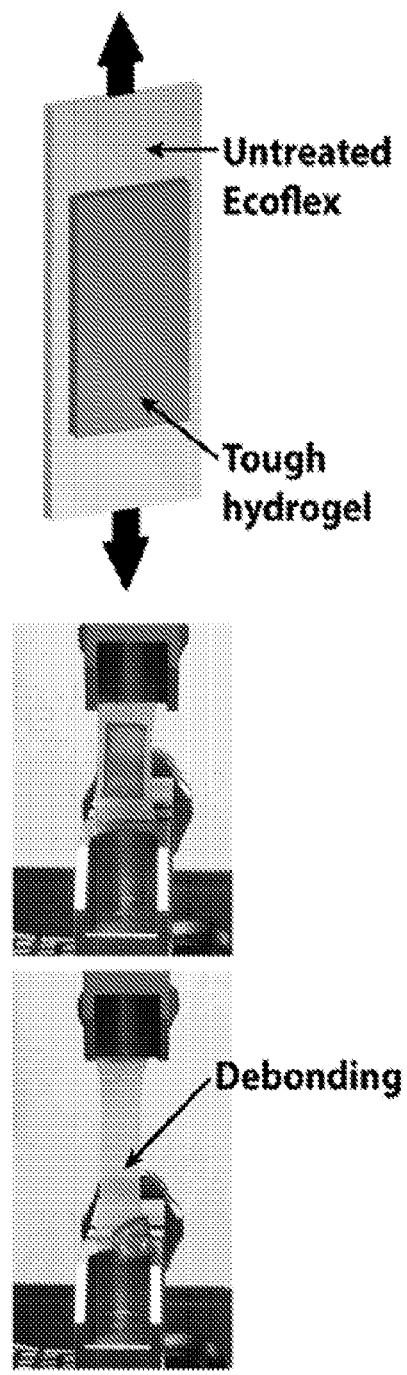
Figure 8:
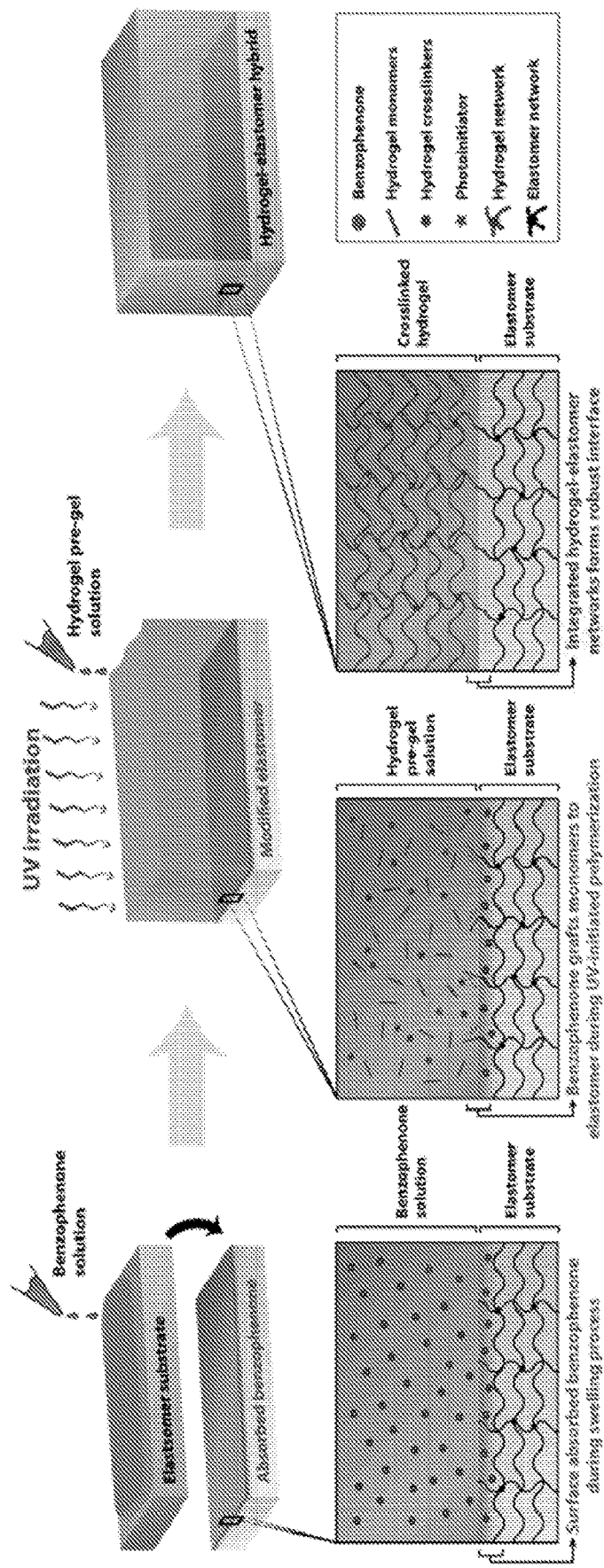
FIG. 8 shows schematics of an alternative fabrication approach for robust hydrogel-elastomer hybrid.
Figure 12:
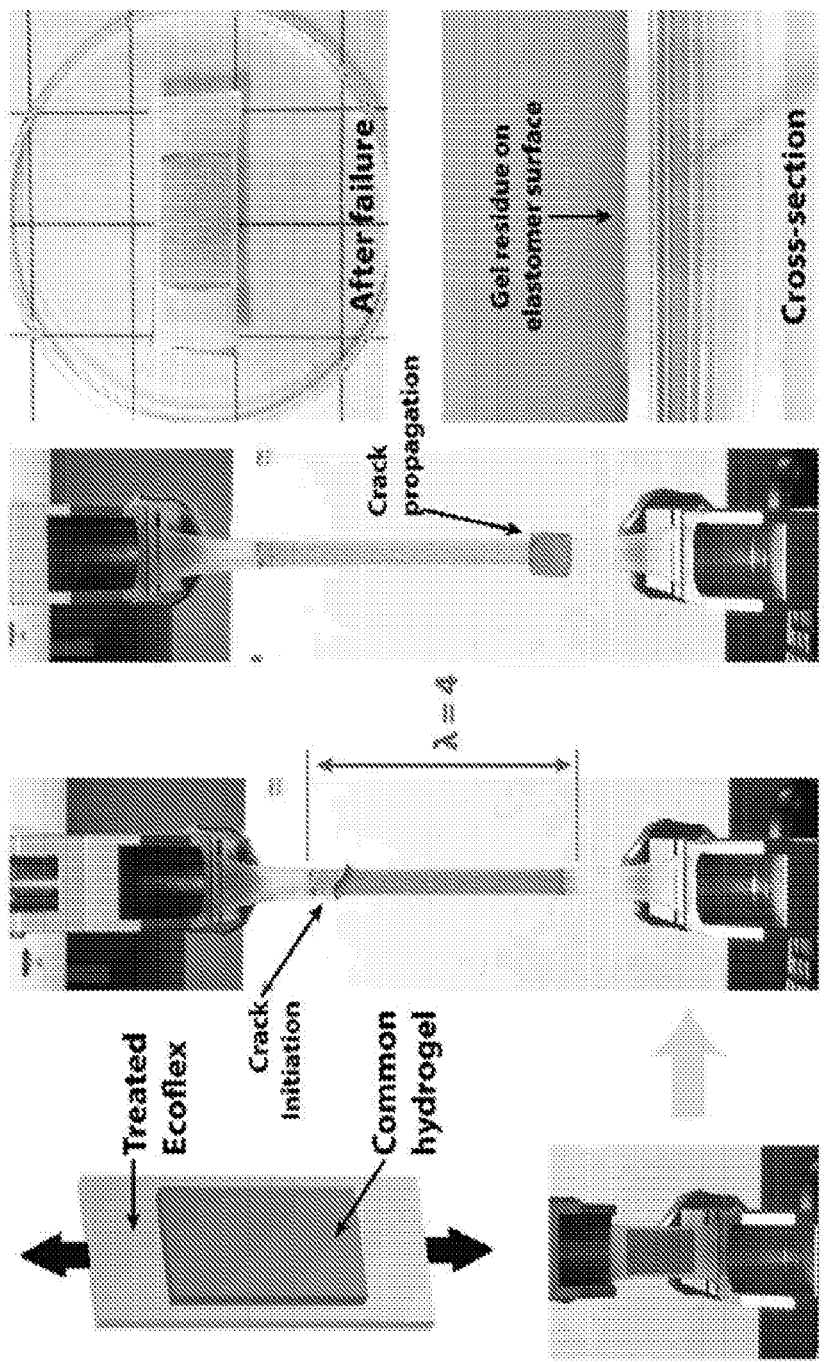
FIG. 12 shows common PAAm hydrogel bonded on Ecoflex® elastomer fails under large deformation (stretch ~4) due to crack propagation in the brittle bulk PAAm hydrogel.

In addition to peeling tests, the high robustness of hydrogel-elastomer hybrids fabricated with the proposed method can also be demonstrated in other modes of deformation. For example, a laminate of PAAm-alginate hydrogel bonded on Ecoflex® sheet can be stretched up to 7 times of its original length without delamination (FIG. 3A). The laminate is fractured under further increased stretch (i.e., stretch ~7.1), but the hydrogel-elastomer interface remains intact without debonding (FIG. 3A). The robust hydrogel-elastomer bonding is intact even after fracture of the hybrid. In contrast, the PAAm-alginate hydrogel adhered on Ecoflex® elastomer untreated by benzophenone detaches from the elastomer under very small deformation (i.e., stretch ~1.1) (FIG. 3B), demonstrating the critical role of benzophenone in achieving robust hydrogel-elastomer interfaces. Note that red food dyes are added into the hydrogels to enhance the contrast between hydrogels and elastomers. Interestingly, common PAAm hydrogel bonded on elastomers treated by benzophenone using a similar method (FIG. 8) can also sustain a relatively high stretch up to 4 times until crack propagation within the brittle bulk hydrogel (FIG. 12). Hydrogel can form robust bonding onto elastomers by directly curing hydrogel precursor onto benzophenone absorbed elastomer surfaces followed by UV irradiation.

Novel Applications of Robust Hydrogel-Elastomer Hybrids.

Figure 4A:
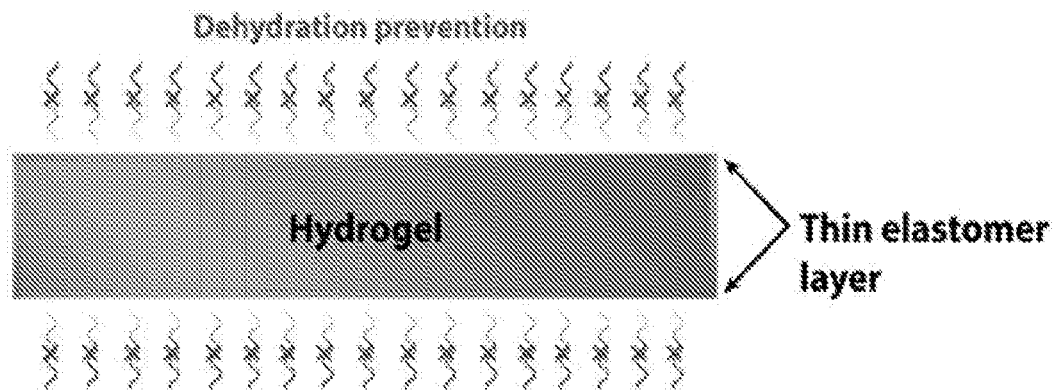
FIGS. 4A-4C show anti-dehydration hydrogel-elastomer hybrid.
Figure 4B:
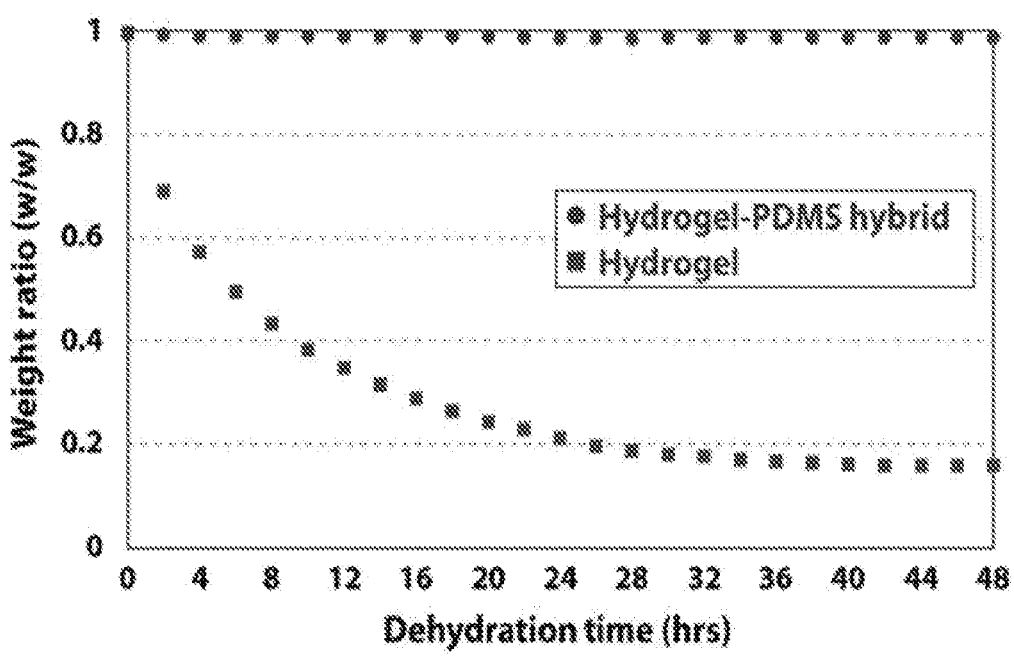
Figure 4C:
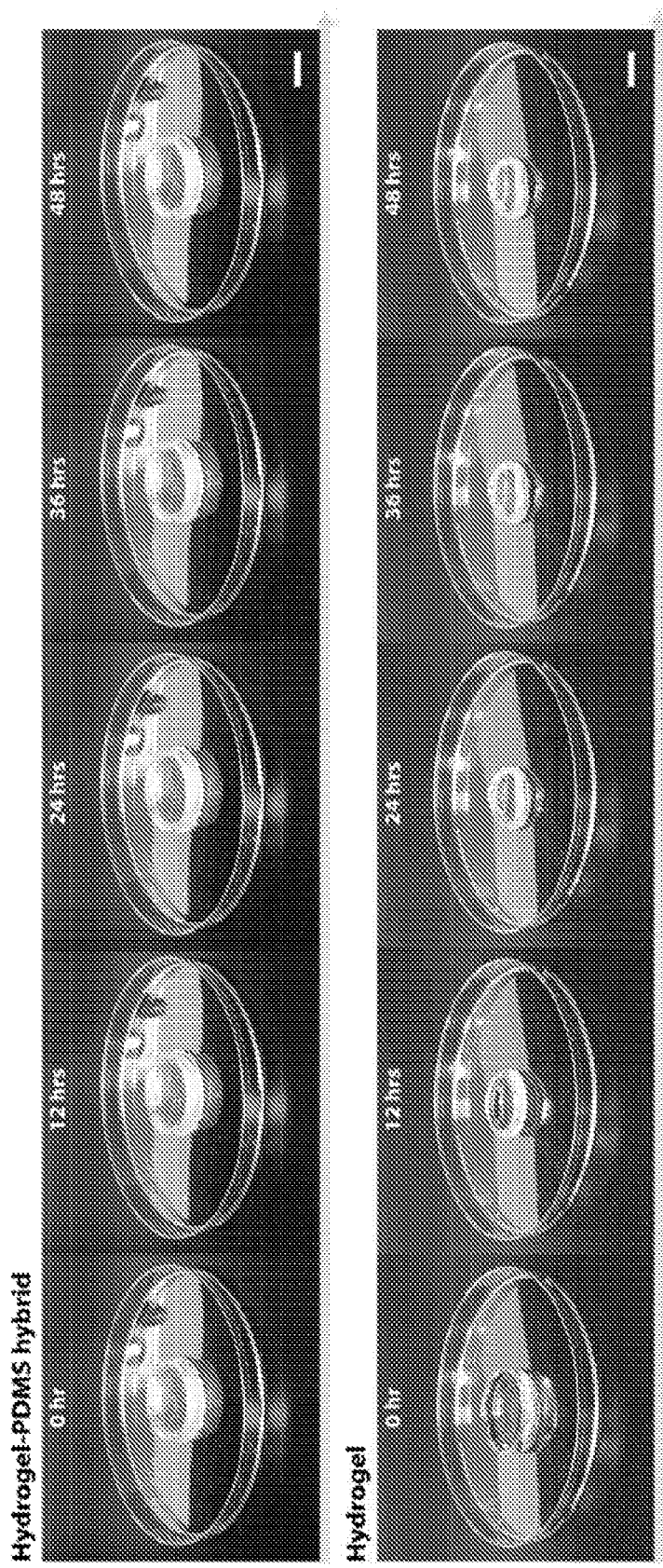

The robust hydrogel-elastomer hybrids enable us to explore various novel applications otherwise unachievable with hydrogel or elastomer systems alone. For instance, with recent development of hydrogel-based devices and machines, the dehydration of hydrogels in dry environments becomes a critical challenge in the field. See, Bai, Y. Transparent hydrogel with enhanced water retention capacity by introducing highly hydratable salt. *Appl. Phys. Lett.* 105, 151903 (2014), which is incorporated by reference in its entirety. On the other hand, the elastomer-like epidermis in mammalian skin can effectively prevent the hydrogel-like body it covers from dehydration. Inspired by the function of epidermis, thin elastomer films was robustly bonded on hydrogels to form anti-dehydration hydrogel-elastomer hybrids (FIG. 4). To test the hypothesis, very thin (~200 µm) PDMS coatings were applied on a PAAm-alginate hydrogel disk (25 mm diameter and 6 mm of thickness) using the proposed fabrication method (FIG. 4A). A very thin layer of PDMS elastomer robustly bonded to the hydrogel can effectively prevent evaporation of water from the hydrogel. Thereafter, dehydration tests were carried out on the hydrogel-elastomer hybrid and an uncoated PAAm-alginate hydrogel with the same dimensions under ambient conditions (24° C. and 19% humidity) for 48 hours (FIG. 4C). The hydrogel-PDMS hybrid did not exhibit noticeable change in its weight over 48 hours while the uncoated hydrogel loses its weight close to its original water contents (~85 wt. %) after 48 hours, demonstrating the effective anti-dehydration of the hydrogel-elastomer hybrids (FIGS. 4B and 4C).

Figure 5A:
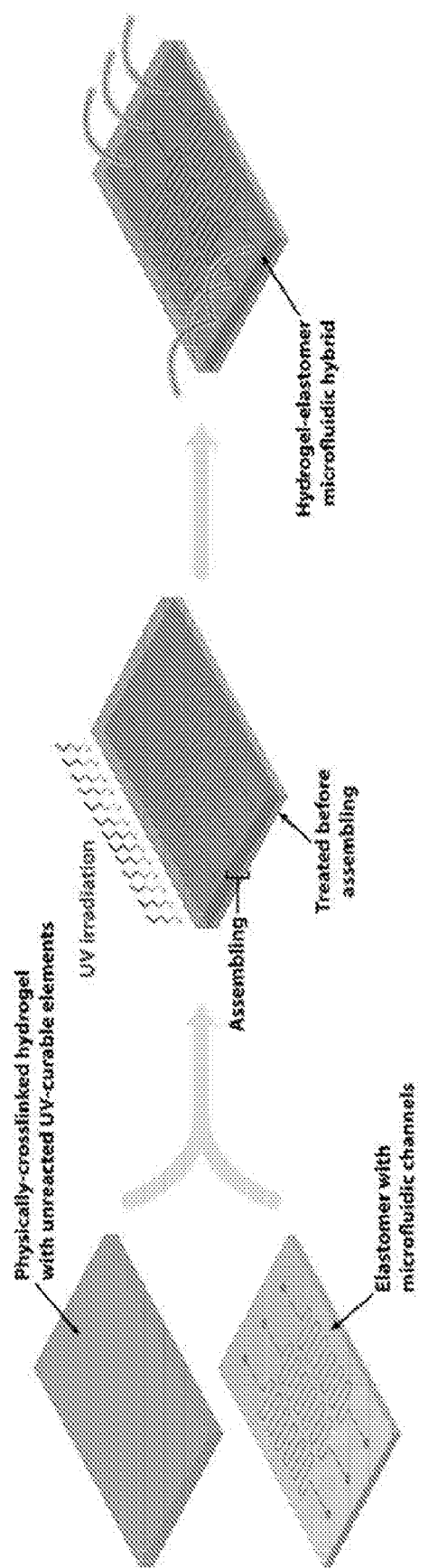
FIGS. 5A-5D show stretchable diffusive and reactive microfluidic chips based on hydrogel-elastomer hybrids.
Figure 5B:
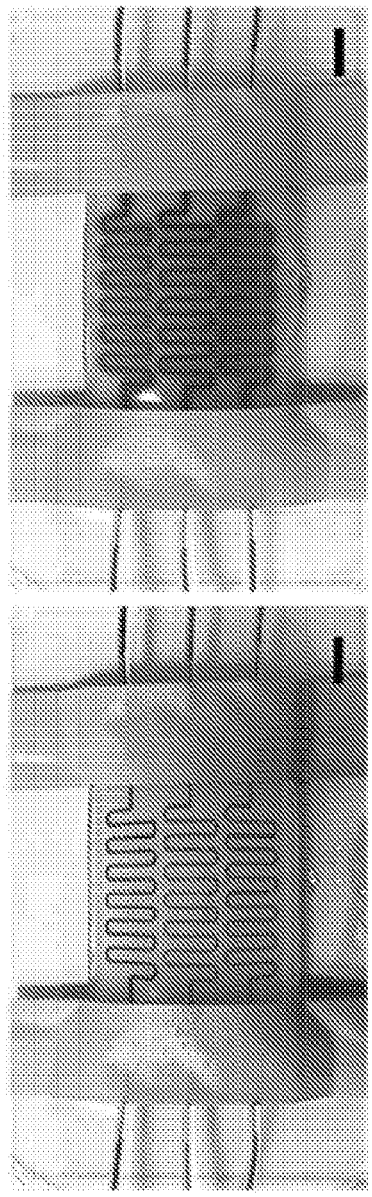
Figure 5C:
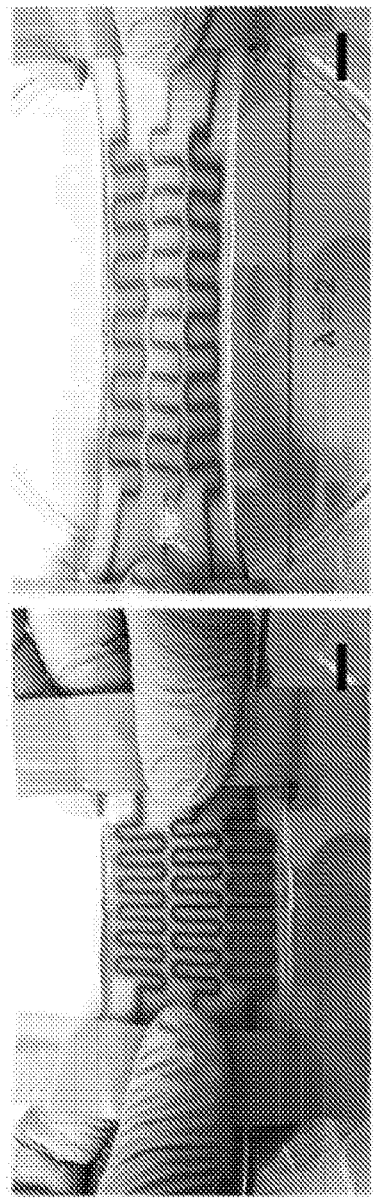
Figure 5D:
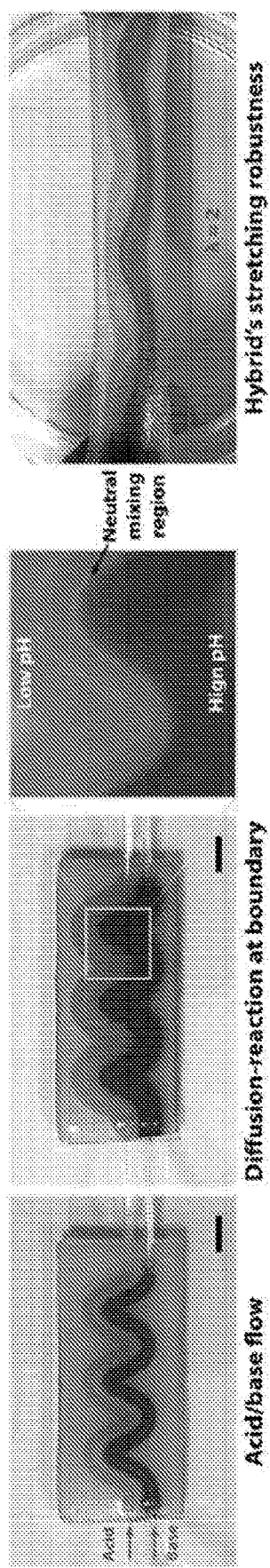
Figure 6A:
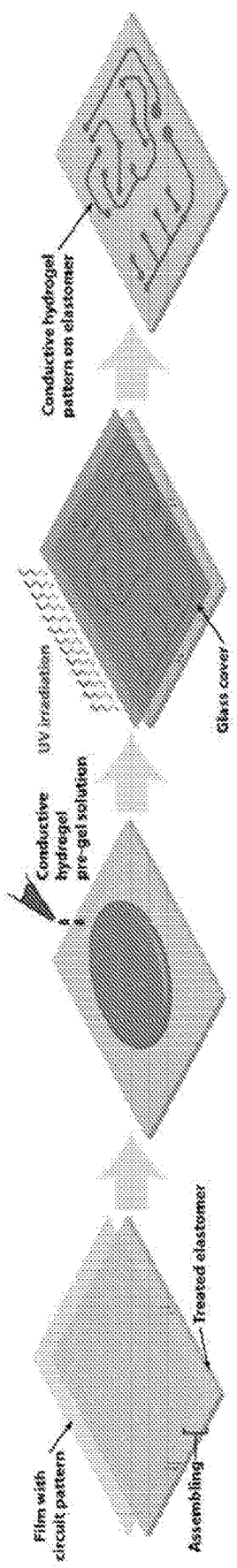
FIG. 6A-6D shows stretchable hydrogel circuit board patterned on elastomer.
Figure 6B:
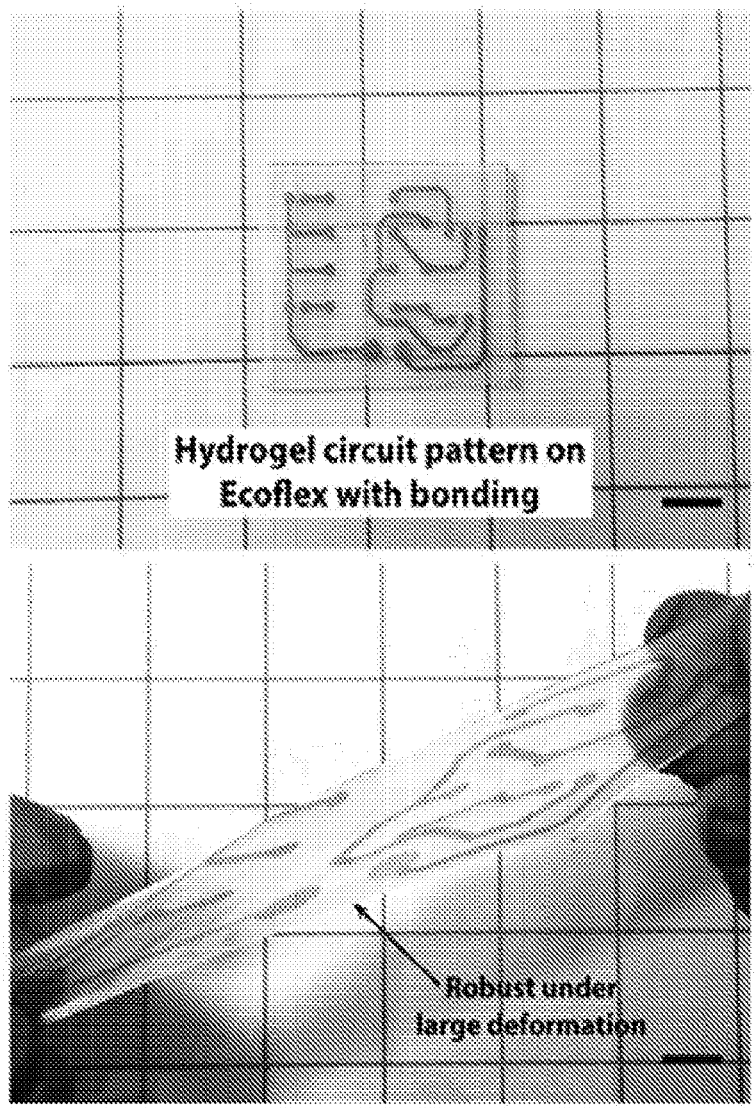
Figure 6C:
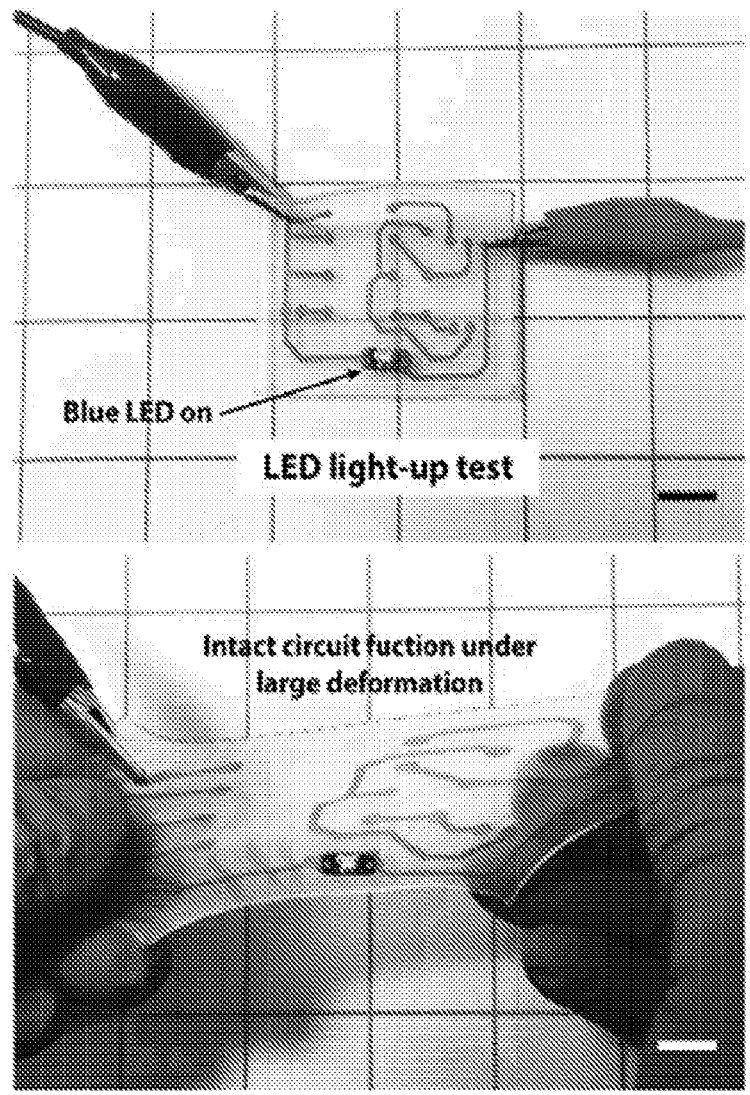
Figure 6D:
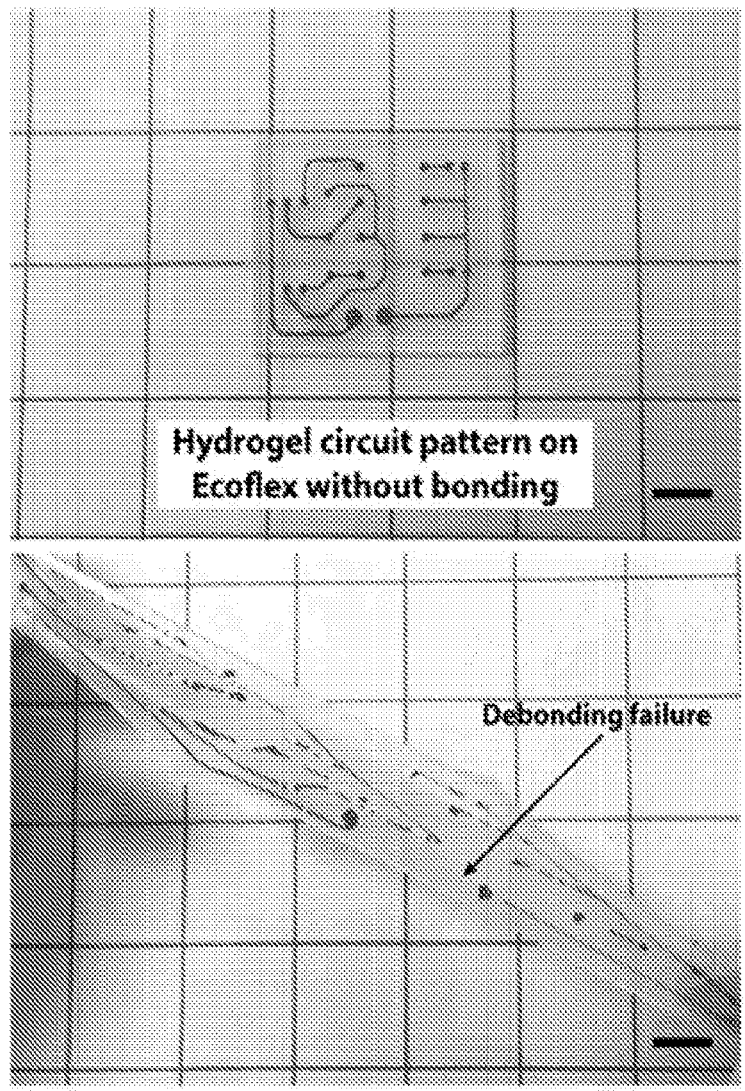

In mammalian skin, the blood and lymphatic vessels in the hydrogel-like dermis provide functions of nourishment and waste removal through a combination of convention and diffusion. Inspired by the functions of micro-vessels in skin, robust yet flexible hydrogel-elastomer hybrids were developed with patterned micro-channels on interfaces to enable simultaneous convection, diffusion and reaction of different species in the hybrids under large deformation (FIGS. 5A-5D). Following the proposed method, diffusive PAAm-alginate hydrogel sheet and flexible Ecoflex® elastomer were assembled with microfluidic channels into robust integrated hybrids (FIG. 5A). The resultant robust and highly stretchable hybrid works as a functional microfluidic assembly with unique features such as convection of solvents in the microfluidic channels plus diffusion through the hydrogel part (FIG. 5B). Notably, the robust interfacial bonding achieved by the proposed method enables large deformation of the hydrogel-elastomer hybrid without failure or debonding-driven leakage of solvents (FIG. 5C). In addition, diffusion-reaction test was carried out through wavy microfluidic channels on Ecoflex® assembled with PAAm-alginate hydrogel that contains pH-indicating molecules (see Materials and Methods for details on fabrication) (FIG. 5D). Acid (pH ~3) and base (pH ~10) solutions from two microfluidic channels can diffuse in the pH-sensitive hydrogel and form regions of different colors (light red indicating acid and dark violet indicating base). The reaction of acid and base solutions further forms a neutral region in the hydrogel (pH ~7, light green color) (FIG. 5D).

As another example, a robust and conductive hydrogel circuit was demonstrated on flexible elastomer substrate (FIG. 6). Conductive hydrogels have been used in transparent electroactive speaker, sensors and electrical signal transmission, but unreliable integration of conductive hydrogels to elastomers greatly limits their applications and reliability. To address the challenge, the proposed fabrication method was utilized to form robust ionically conductive hydrogel circuit patterned on top of thin Ecoflex® substrate that mimics printed circuit board (PCB) for standard electronics (FIG. 6A). FIG. 6B shows that the hydrogel circuit fabricated by the proposed method can sustain large deformation and high stretch without noticeable failure. In FIG. 6C, the functionality of the fabricated hydrogel circuit board is demonstrated by lighting up LED with an AC power source connected to the hydrogel circuit. The conductive hydrogel circuit can indeed maintain its electrical functionality even under severe deformation (FIG. 6C). To validate the importance of robust hydrogel-elastomer interfaces for such hydrogel circuit, a control test was performed by deforming the same ionically conductive hydrogel circuit patterned on elastomer substrate without benzophenone treatment (i.e., weak interfaces) (FIG. 6D). The hydrogel pattern without robust interface easily debonds from the elastomer substrate and fails under deformation, indicating the importance of robust bonding of hydrogel on elastomer substrates for the stretchable hydrogel circuits (FIG. 6D).

Natural hybrids of hydrogel-like dermis and elastomer-like epidermis in mammalian skins possess robust interfaces and functional microstructures that have not been achieved in synthetic hydrogel-elastomer systems. A method described herein can create synthetic hydrogel-elastomer hybrids with interfacial bonding tougher than epidermis-dermis interfaces and functional micro-channels and micro-patterns inspired by blood and lymphatic vessels in mammalian skins. The method integrates three innovations in fabrication of soft hybrids: i.) pre-shaping both elastomers and hydrogels before bonding to conserve their microstructures; ii.) modification of cured elastomer surfaces with benzophenone for chemical bonding with hydrogels; and iii) harnessing dissipative properties of tough hydrogels to achieve robust interfaces. The method is widely applicable to various commonly-used elastomers including PDMS Sylgard® 184, polyurethane, latex, VHB™ and Ecoflex® and tough hydrogels including PAAm-algiante, PAAm-hyaluronan, PAAm-chitosan, PEGDA-alginate and PEGDA-hyaluronan. The robust hydrogel-elastomer hybrids allow us to harness distinctive but complementary advantages of both elastomers and hydrogels and explore novel applications including anti-dehydration hydrogels, stretchable diffusive and reactive microfluidic chips, and stretchable hydrogel circuit board.

In addition, the ability to fabricate extremely robust and microstructured hydrogel-elastomer hybrids makes a number of future research directions and applications possible. For example, elastomer-based flexible electronic devices integrated with hydrogels may lead to development of a new class of flexible bio-electronic devices for seamless interfacing between human body and engineering devices. Biocompatible and/or biodegradable hydrogels containing living organisms (e.g., bacteria and cells) integrated with existing elastomer-based devices may be a promising route toward more creative utilization of living organisms for engineering applications. See, Feinberg, A. W. et al. Muscular thin films for building actuators and powering devices. *Science* 317, 1366-1370 (2007), Nawroth, J. C. et al. A tissue-engineered jellyfish with biomimetic propulsion. *Nature biotechnology* 30, 792-797 (2012), and Chen, A. Y., Zhong, C. & Lu, T. K. Engineering living functional materials. *ACS synthetic biology* 4, 8-11 (2015), each of which is incorporated by reference in its entirety. Microfluidic systems based on hydrogel-elastomer hybrids may provide more efficient platforms for diverse biomedical studies owning to its unique integration of convention, diffusion, reaction and deformation.

EXAMPLES

Materials.

Unless otherwise specified, the chemicals used in the current work were purchased from Sigma-Aldrich and used without further purification. For the covalently-crosslinked stretchy polymer networks in the tough hydrogels, acrylamide (AAm; Sigma-Aldrich A8887) was the monomer used for the polyacrylamide (PAAm) networks, and 20 kDa polyethylene glycol diacrylate (PEGDA; Sigma-Aldrich 767549) was the macromonomer used for the PEGDA networks. For the polyacrylamide (PAAm) hydrogel, N,N-methylenebisacrylamide (MBAA; Sigma-Aldrich 146072) was used as crosslinker and 2-Hydroxy-4'-(2-hydroxyethoxy)-2-methylpropiophenone (Irgacure 2959; Sigma-Aldrich 410896) was used as photoinitiator. For the PEGDA hydrogel, Irgacure 2959 was used as photoinitiator. For the physically-crosslinked dissipative polymer networks in the tough hydrogels, a number of ionically crosslinkable biopolymers were used including sodium alginate (Sigma-Aldrich A2033) ionically-crosslinked with calcium sulfate (Sigma-Alginate C3771), chitosan (Sigma-Aldrich 448869) ionically-crosslinked with sodium tripolyphosphate (TPP; Sigma-Aldrich 238503), and sodium hyaluronan (HA; Sigma-Aldrich H5542) ionically-crosslinked with iron chloride (Sigma-Aldrich 157740). For elastomer surface treatment, benzophenone (Sigma-Aldrich B9300) was used. To visualize pH change within hydrogel-elastomer microfluidic assembly, universal pH indicator solution (Sigma-Aldrich 36828), hydrogen chloride (HCl; Sigma-Aldrich 38280) and sodium hydroxide (NaOH; Sigma-Aldrich 795429) were used.

For elastomers, Sylgard® 184 (PDMS; Dow Corning), Ecoflex® (Smooth-On), polyurethane (Smooth-On), latex (McMaster Carr) and VHB™ (3M) were used. In the 90-degree peeling experiments, borosilicate glass (McMaster Carr) was used as rigid substrate together with elastomers. As a stiff backing for the hydrogel sheet, polyethylene terephthalate (PETE) film (70 µm; ePlastics) were used together with cyanoacrylate (Loctite, Henkel). In the conductive hydrogel PCB pattern experiments, sodium chloride (Sigma-Aldrich 746398) solution was used as an electrolyte. For hydrophobic coating of glass molds and covers, Rain-X (ITW Inc.) solution was used.

Hydrogel Bonding on Elastomers.

Surface treated elastomers were prepared by introducing surface absorbed benzophenone on elastomer surfaces. Elastomer surfaces were thoroughly cleaned with methanol and deionized water, and completely dried with nitrogen gas before the next step. Benzophenone solution (10% in ethanol) was applied onto elastomer evenly covering the entire surface and incubated for 2 minutes at room temperature. Then, substrates were washed with methanol three times and completely dried with nitrogen gas. Each elastomer substrates were freshly treated before each hydrogel bonding experiments to avoid unwanted diffusion of benzophenone into elastomer matrix. See, Schneider, M. H., Tran, Y. & Tabeling, P. Benzophenone absorption and diffusion in poly (dimethylsiloxane) and its role in graft photo-polymerization for surface modification. *Langmuir* 27, 1232-1240 (2011), which is incorporated by reference in its entirety.

Physically-crosslinked hydrogel was prepared by mixing 10 mL of a carefully degassed aqueous pre-gel solution (12.05 wt. % AAm, 1.95 wt. % sodium alginate and 0.017 wt. % MBAA for the PAAm-alginate hydrogel; 18 wt. % AAm, 2 wt. % HA and 0.026 wt. % MBAA for the PAAm-hyaluronan hydrogel; 24 wt. % AAm, 2 wt. % chitosan and 0.034 wt. % MBAA for the PAAm-chitosan hydrogel; 20 wt. % PEGDA and 2.5 wt. % sodium alginate for the PEGDA-alginate hydrogel; 20 wt. % PEGDA and 2 wt. % HA for the PEGDA-hyaluronan hydrogel) with ionic crosslinkers ($20 \times 10^{-3}$ M concentration of calcium sulfate in the PAAm-alginate hydrogel; $3 \times 10^{-3}$ M concentration of iron chloride in the PAAm-hyaluronan hydrogel; $3 \times 10^{-3}$ M concentration of TPP in the PAAm-chitosan hydrogel; $20 \times 10^{-3}$ M concentration of calcium sulfate in the PEGDA-alginate hydrogel; $3 \times 10^{-3}$ M concentration of iron chloride in the PEGDA-hyaluronan hydrogel) and Irgacure 2959 (0.2 wt. %). The mixture was mixed quickly and poured onto glass mold, and covered by glass plate with hydrophobic coating. The hydrogel was kept in nitrogen chamber for 1 hour before the next step. Then, the physically-crosslinked hydrogel was gently removed from the mold and assembled with freshly treated elastomer followed by UV irradiation inside UV crosslinker (365 nm UV; UVP CL-1000) for an hour during which PAAm network crosslinking and bonding onto elastomer surface occurred.

PAAm common hydrogel was prepared by directly curing the degassed pre-gel solution (23 wt. % AAm, 0.051 wt. % MBAA and 0.2 wt. % Irgacure 2959) onto freshly treated elastomer surface inside UV crosslinker. The crosslinking condition was identical to the PAAm-alginate hydrogel. Note that the shear moduli of the PAAm hydrogel was tuned to match the PAAm-alginate hydrogel's modulus (30 kPa) based on the previously reported data. See, Sun, J.-Y. et al. Highly stretchable and tough hydrogels. *Nature* 489, 133-136 (2012), which is incorporated by reference in its entirety.

Mechanical Testing.

All tests were conducted in ambient air at room temperature. The hydrogels and hydrogel-elastomer interfaces maintained consistent properties over the time of the tests (i.e., ~a few minutes), during which the effect of dehydration is not significant. The interfacial toughness of various hydrogel-elastomer hybrids was measured using the standard 90-degree peeling test (ASTM D 2861) with mechanical testing machine (2 kN or 20 N load cells; Zwick/Roell Z2.5) and 90-degree peeling fixture (Test Resources, G50). All elastomer substrates were prepared with 2.5 cm in width, 7.5 cm in length and 1 mm in thickness. PDMS and Ecoflex® were adhered on borosilicate glass plate using oxygen plasma treatment (Harrick Plasma PDC-001). Latex and polyurethane were adhered on glass plate by using epoxy adhesives. VHB™ was simply adhered onto glass plate as it was provided in two-sided tape form. Hydrogels were bonded onto elastomer surface by following the above procedure with the size of 100 mm×15 mm×3 mm (length×width× thickness). A stiff backing is introduced to prevent elongation of hydrogel sheet along the peeling direction. As a stiff backing for the hydrogel, PETE film was used with cyanoacrylate adhesive to bond them onto hydrogels. Prepared samples were tested with the standard 90-degree peeling test with constant peeling speed of 50 mm/min. The measured force reached a plateau as the peeling process entered steady state, and this plateau force was calculated by averaging the measured force values in the steady state region with MATLAB. The interfacial toughness was determined by dividing the plateau force F by the width of the hydrogel sheet W.

For the stretching test of hydrogel-elastomer hybrids, PAAm-alginate tough hydrogel and PAAm common hydrogel with size of 50 mm×20 mm×3 mm (length×width× thickness) were bonded onto Ecoflex® substrate following the abovementioned procedure. For physically-attached samples, the same size of PAAm-alginate tough hydrogel was simply put onto the Ecoflex® substrate without any other treatment. The stretching of hybrids was carried out using the mechanical testing machine (2 kN; Zwick/Roell Z2.5) with grip-to-grip separation speed of 100 mm/min.

Numerical Modeling and Simulation of 90-Degree Peeling of Hydrogel.

A two-dimensional (2D) finite-element model was developed to simulate the 90-degree-peeling test of hydrogels bonded on diverse elastomer substrates (i.e., Sylgard® 184 PDMS, polyurethane, latex, VHB™ and Ecoflex®). A hydrogel strip with length 80 mm and thickness 3 mm was adhered on an elastomer sheet, where the 0.2 mm thin residual hydrogel layer was assumed on the elastomer substrate which is connected to the bulk hydrogel via cohesive element (FIG. 13). The yellow line indicates the stiff backing and the red line indicates the cohesive element between bulk hydrogel sheet and the thin residual hydrogel layer on various elastomer substrates.

The deformation of the hydrogel strip was assumed to be under plane-strain condition. The elastic properties and energy dissipation of the hydrogel were modeled as the Ogden hyperelastic material and Mullins effect, respectively. See, Ogden, R. & Roxburgh, D. A pseudo-elastic model for the Mullins effect in filled rubber. *Proc. R. Soc. Lond. Ser. A* 455, 2861-2877 (1999), which is incorporated by reference in its entirety. The parameters of the model were obtained from the previous studies on the PAAm-alginate hydrogel. See, Sun, J.-Y. et al. Highly stretchable and tough hydrogels. *Nature* 489, 133-136 (2012), and Yuk, H., Zhang, T., Lin, S., Parada, G. A. & Zhao, X. Tough bonding of hydrogels to diverse non-porous surfaces. *Nat Mater*, 15, 190-196 (2016), each of which is incorporated by reference in its entirety. For the elastic properties, the one-term Ogden model can be expressed as $$U_{ela} = 2\mu/\alpha^2(\lambda_1^\alpha + \lambda_2^\alpha + \lambda_3^\alpha - 3)$$

where $U_{ela}$ is the strain energy density, $\lambda_i$ the $i_{th}$ principal stretch, $\mu$ the shear modulus (fitted to be 36.57 kPa), and $\alpha$ the Ogden parameter (fitted to be 1.473). The theoretical model for the Mullins effect can be expressed as $$U = \eta \tilde{U}_{ela} + \phi(\eta)$$

$$\phi(\eta) = \int_1^\eta [(m + \beta U_{ela}^m)\text{erf}^{-1}(r(1-\eta)) - U_{ela}^m]d\eta$$

$$\eta = 1 - \frac{1}{r}\text{erf}\left[(U_{ela}^m - \tilde{U}_{ela})/(m + \beta U_{ela}^m)\right]$$

where $\eta$ is a damage variable ($0 < \eta \leq 1$) $\tilde{U}_{ela}$ is the strain energy density of perfectly elastic material (i.e., the primary loading path is also the unloading path), $U_{ela}^m$ denotes the maximum strain energy density before unloading, the function $\phi(\eta)$ is referred to as the damage function, erf is the error function, and the material parameters r=1.1, m=4.076, and β=0.2818 were obtained by fitting the model to measured stress-strain hysteresis of the PAAm-alginate hydrogel (FIG. 14). See, Sun, J.-Y. et al. Highly stretchable and tough hydrogels. *Nature* 489, 133-136 (2012), which is incorporated by reference in its entirety. The elastomer substrates were assumed to be elastic materials which were modeled as the Neo-Hookean model, corresponding to an Ogden hyperelastic material with the Ogden parameter of 2 and shear moduli of 0.6 MPa (Sylgard® 184 PDMS); 30 kPa (Ecoflex®); 1.6 MPa (polyurethane); 1 MPa (latex); 0.6 MPa (VHB™).

The stiff backing was modeled as a linear elastic material with very high Young's modulus (i.e., 2 GPa) and very low thickness (i.e., 100 µm). The cohesive layer on the interface was characterized by a triangular cohesive law with maximum strength $S_{max}$ and maximum separation distance $\delta_{max}$. The damage of the cohesive layer follows the quadratic nominal stress criterion, $$\left\{\frac{t_n}{S_{max}}\right\}^2 + \left\{\frac{t_s}{S_{max}}\right\}^2 = 1$$

where $t_i(n, s)$ represents the nominal stress, and the subscript n and s indicate deformation normal to and tangential to the interface respectively.

All the numerical simulations were carried out with ABAQUS/Explicit. The hydrogel, stiff backing and elastomer were modeled with CPE4R element, and the cohesive layer at the interface was modeled with COH2D element. The Poisson's ratios of the hydrogel and elastomer were set to be 0.499 to approximate incompressibility. The adhesive interface was uniformly discretized with very fine mesh size (0.1 mm). Mass scaling technique was adopted to maintain a quasi-static process during the peeling simulations. To simulate the peeling test described in the material and experiment section, the left edge of the strip was first rotated 90-degrees and then moved vertically at a constant velocity, with the reaction force on the left edge of the strip recorded. During the simulations, the bottom surface of the elastomer is fixed to mimic the constraint of the rigid glass substrate used in experiments. The interfacial toughness was then calculated as the steady-state reaction force divided by the width of the strip, which is set to be unity in the current model. The parameters for cohesive element between the bulk hydrogel slap and the residual layer are chosen as $S_{max}$ equal to 200 kPa and $\delta_{max}$ to be 3.0 mm which gives the intrinsic work of adhesion $\Gamma_0$ of 300 $Jm^{-2}$ for the hydrogel adhesion on the elastomer substrate under the situation of cohesive failure of the hydrogel.

Preparation and Testing of Anti-Dehydration Coating.

Thin PDMS layer was prepared by spin-coating Sylgard® 184 resin on acrylic plate (500 rpm for 60 seconds) with final thickness around 200 microns. Prepared thin PDMS film was placed on inner surfaces of glass mold with the dimension of 25 mm diameter and 6 mm of thickness. PDMS film inside glass mold was treated with benzophenone solution following the previously described procedure. Then, Hydrogel-PDMS hybrid was prepared by pouring PAAm-alginate hydrogel pre-gel solution into the PDMS-covered mold followed by UV irradiation. Hydrogel without anti-dehydration coating was prepared by crosslinking PAAm-alginate pre-gel solution using the same glass mold without PDMS film. The dehydration tests were carried out at room temperature with low humidity (24° C. and 19% humidity) for 48 hours. Weight change of the samples during dehydration tests was recorded every 2 hours for comparison.

Preparation and Testing of Hydrogel-Elastomer Microfluidic Assembly.

Ecoflex® microfluidic channel was prepared by curing Ecoflex® resin onto silicon wafer mold with predetermined positive SU-8 patterns following conventional soft lithography techniques. See, Xia, Y. & Whitesides, G. M. Soft lithography. *Annual review of materials science* 28, 153-184 (1998), which is incorporated by reference in its entirety. Physically-crosslinked PAAm-alginate hydrogel slab was prepared by the previously described procedure. Physically-crosslinked PAAm-algiante hydrogel was gently assembled on top of Ecoflex® microfluidic channel, then the assembly was exposed to UV irradiation inside UV crosslinker for an hour. To verify microfluidic function and diffusion through hydrogel matrix, 2% aqueous solution of red, blue and green food dye (McCormick) were supplied through three channel inlets respectively.

The microfluidic hybrid for the diffusion-mixing test was prepared following the same steps as like the prior case except that 0.1 wt. % of universal pH indicator solution was added into PAAm-alginate pre-gel solution. To test diffusion-based mixing of waterborne chemicals, acid solution (0.1 M aqueous HCl solution) and base solution (0.1 M aqueous NaOH solution) were supplied in each channels. Note that all hydrogel-elastomer microfluidic hybrids were kept in humid chamber during tests to avoid dehydration.

Preparation and Testing of Conductive Hydrogel Pattern on Elastomer.

To form conductive hydrogel circuit board pattern on Ecoflex® substrate, thin PETE film (70 μm thickness) with predetermined circuit board pattern was prepared using laser cut machine (Epilog Mini/Helix). As a template for hydrogel pattern on elastomer, the film with circuit board pattern was assembled with thin Ecoflex® substrate (1 mm thickness) treated with benzophenone solution as previously described. Then, PAAm-alginate pre-gel solution was poured onto the assembly and covered with glass cover followed by UV irradiation for an hour. After UV irradiation procedure, the glass cover and the PETE film were removed from the Ecoflex® substrate leaving robustly bonded PAAm-alginate hydrogel pattern. The hydrogel pattern was made ionically conductive by submerging the hybrid in concentrated sodium chloride solution (3 M) for 6 hours. To light up a LED on the conductive hydrogel circuit pattern, each ends of pattern were connected to a functional generator (5 V peak-to-peak voltage at 1 kHz).

Other embodiments are within the scope of the following claims.

What is claimed is:

1. A composition comprising:
   an elastomer substrate;
   one or more surfaces of the elastomer substrate modified by a surface absorbed initiator; and
   a hydrogel layer disposed on the one or more surfaces of the elastomer substrate modified by the surface absorbed initiator;
   wherein the hydrogel layer and the one or more surfaces of the elastomer substrate modified by the surface absorbed initiator are hybridized via covalent crosslinking.

2. The composition of claim 1, wherein the surface absorbed initiator is a photoinitiator.

3. The composition of claim 2, wherein the photoinitiator is benzophenone.

4. The composition of claim 1, wherein the hydrogel includes a physically-crosslinked polymer network.

5. The composition of claim 1, wherein the elastomer substrate includes a chemically-crosslinked polymer network.

6. The composition of claim 4, wherein the physically-crosslinked polymer network includes a polymer selected from a group consisting of alginate, hyaluronan, and chitosan.

7. The composition of claim 5, wherein the chemically-crosslinked polymer network includes a polymer selected from a group consisting of polyacrylamide, polyethylene glycol diacrylate, polydimethylacrylamide, poly (N-isopropylacrylamide), and poly (2-hydroxyethyl methacrylate).

8. The composition of claim 1, wherein the elastomer substrate includes microfluidic channels.

9. The composition of claim 1, wherein the hydrogel layer forms a first layer, the elastomer substrate forms a second layer, and wherein the composition further comprises a third layer, the third layer comprising an elastomer layer, wherein the first layer is positioned between the second layer and the third layer.

10. The composition of claim 9, wherein the third layer is hybridized with the first layer via covalent crosslinking.

11. The composition of claim 1, wherein the hydrogel layer forms a first layer, the elastomer substrate forms a second layer, and wherein the composition further comprises a third layer including an electrical circuit pattern, wherein the third layer is positioned between the first layer and the second layer.

12. The composition of claim 11, wherein the first layer includes a conductive hydrogel.

13. A coating including the composition of claim 1.

14. A device including the coating of claim 13.

15. A sensor including the coating of claim 13.

16. The composition of claim 2, wherein the surface absorbed initiator is selected from benzophenone, benzoin ethyl ether, benzoin isobutyl ether, benzoin methyl ether, 4,4'-bis(diethylamino)benzophenone and 4,4'-Bis(dimethylamino)benzophenone.

17. The composition of claim 1, wherein the surface absorbed initiator is a thermal initiator.

18. The composition of claim 17, wherein the thermal initiator is selected from t-butylperoxide, cumyl peroxyneodecanoate and cumyl peroxyneoheptanoate.

* * * * *